United States Patent [19]

Kitamura et al.

[11] Patent Number: 5,830,703
[45] Date of Patent: Nov. 3, 1998

[54] DNA ENCODING ADRENOMEDULLIN

[75] Inventors: Kazuo Kitamura, Miyazaki; Kenji Kangawa, Suita; Hisayuki Matsuo, Kobe; Tanenao Eto, Miyazaki, all of Japan

[73] Assignees: Shionogi & Co., Ltd.; Kenji Kangawa, both of Osaka, Japan

[21] Appl. No.: 801,863

[22] Filed: Feb. 18, 1997

Related U.S. Application Data

[62] Division of Ser. No. 233,389, Apr. 26, 1994, Pat. No. 5,639,855.

[30]     Foreign Application Priority Data

| Apr. 26, 1993 | [JP] | Japan | 5-99856 |
| Jul. 23, 1993 | [JP] | Japan | 5-183107 |
| Nov. 29, 1993 | [JP] | Japan | 5-298736 |
| Apr. 18, 1994 | [JP] | Japan | 6-79035 |

[51] Int. Cl.$^6$ .......................... C12N 15/16; C12N 15/63; C07K 14/47
[52] U.S. Cl. ................ 435/69.4; 435/71.2; 435/172.3; 435/325; 435/252.3; 435/254.11; 435/320.1; 536/23.1; 536/23.5; 536/23.51; 530/324; 530/326; 530/327; 530/328; 530/329; 530/399; 530/402
[58] Field of Search ................ 536/23.1, 23.5, 536/23.51; 435/69.1, 69.4, 71.1, 71.2, 172.3, 325, 252.3, 254.11, 320.1; 530/324, 402, 399, 328, 327, 329, 326

[56]             References Cited

U.S. PATENT DOCUMENTS

| 4,708,934 | 11/1987 | Gilligan et al. | 435/68 |
| 5,552,520 | 9/1996 | Kim et al. | 530/311 |

FOREIGN PATENT DOCUMENTS 4-282399   10/1992   Japan .

OTHER PUBLICATIONS

W. Burgess et al., "Possible Dissociation of the Heparin–binding and Mitogenic Activities of Heparin–binding (Acidic Fibroblast) Growth Factor–1 from its Receptor–binding Activities by Site–directed Mutagenesis of a Single Lysine Residue", *J. of Cell Biology*, V. III, pp. 2129–2138 (1990).

H. Geysen et al., "Strategies for Epitope Analysis Using Peptide Synthesis", *J. Immunological Methods*, 102, pp. 259–274 (1987).

E. Lazar et al., "Transforming Growth Factor α: Mutation of Aspartic Acid 47 and Leucine 48 Result in Different Biological Activities", *Molecular and Cellular Biology*, vol. 8, No. 3, pp. 1247–1252 (1988).

C. Nuki et al., "Vasodilator Effect of Adrenomedullin and Calicitonin Gene–related Peptide Receptors in Rat Mesenteric Vascular Beds", *Biochem. Biophys. Res. Commun.*, vol. 196, pp. 245–251 (1993).

J. Sakata et al., "Molecular Cloning and Biological Activities of Rat Adrenomedullin, a Hypotensive Peptide", *Biochem. Biophys. Res. Commun.*, vol. 195, pp. 921–927 (1993).

G. Cooper et al, "Purification and Characterization of a Peptide from Amyloid–rich Pancreases of Type 2 Diabetic Patients", *Proc. Natl. Acad. Sci. USA*, 84, pp. 8628–8632 (1987).

Q. Hao et al., "An Adrenomedullin (ADM) Fragment Retains the Systemic Vasodilator Activity of Human ADM", *Life Sci.*, 54, pp. PL 265–270 (1994).

K. Kangawa & H. Matsuo, "Purification and Complete Amino Acid Sequence of α–Human Atrial Natriuretic Polypeptide (α–hANP)", *Biochem. Biophys. Res. Commun.*, 118, pp. 131–139 (1984).

T. Kita et al, "Effects of Brain Natriuretic Peptide–45, a Circulating Form of Rat Brain Natriuretic Peptide, in Spontaneously Hypertensive Rats", *Eur. J. Pharmacol.*, 202, pp. 73–79 (1991).

K. Kitamura et al, "Isolation and Characterization of Peptides which Act on Rat Platelets, from a Pheochromocytoma", *Biochem. Biophys. Res. Commun.*, 185, pp. 134–141 (1992).

K. Kitamura et al., "Cloning and Characterization of cDNA Encoding a Precursor for Human Adrenomedullin", *Biochem. Biophys. Res. Commun.*, 194, pp. 720–725 (1993).

K. Kitamura et al., "Adrenomedullin: A Novel Hypotensive Peptide Isolated From Human Pheochromocytoma," *Biochem. Biophys. Res. Commun.*, 192, pp. 553–560 (1993).

R. Mains et al., "Strategies for the Biosynthesis of Bioactive Peptides", *Trends Neurosci.*, 6, pp. 229–235 (1993).

K. Mizuno, "Biochemical Studies of Enzymes Involved in Processing of Biologically Active Peptide", *Seikagaku*, 61, pp. 1435–1461 (1989).

H. Morris et al, "Isolation and Characterization of Human Calcitonin Gene–related Peptide", *Nature*, 308, pp. 746–748 (1984).

P. Steenbergh et al, "A Second Human Calcitonin/CGRP Gene", *FEBS Lett.*, 2488, pp. 403–407 (1985).

*Primary Examiner*—John Ulm
*Assistant Examiner*—Prema Mertz
*Attorney, Agent, or Firm*—Fish & Neave; James F. Haley, Jr., Esq.

[57]             ABSTRACT

According to the present invention, adrenomedullin which is a novel peptide having a hypotensive effect; proadrenomedullin N-terminal 20 peptide (proAM-N20) corresponding to an amino acid sequence of an N-terminus of proadrenomedullin, having a catecholamine secretion inhibitory effect; proadrenomedullin N-terminal 10–20 peptide (proAM-N(10–20)) having a Na channel inhibitory effect, and a gene encoding these peptides are provided. In addition, according to the present invention, these peptides in a sample containing adrenomdullin or proAM-N20 in an unknown amount can be quantified by using an antibody against adrenomedullin, proAM-N20, or its fragment.

18 Claims, 4 Drawing Sheets

Fig.1

1                                                                10
Tyr-Arg-Gln-Ser-Met-Asn-Asn-Phe-Gln-Gly-Leu-Arg-Ser-Phe-Gly-
├─RE1─┤ ├─────────────RE2─────────────┤ ├────RE3────

20                                           30
Cys-Arg-Phe-Gly-Thr-Cys-Thr-Val-Gln-Lys-Leu-Ala-His-Gln-Ile-
├────┤ ├──────────────────────────────RE4──────────

40
Tyr-Gln-Phe-Thr-Asp-Lys-Asp-Lys-Asp-Asn-Val-Ala-Pro-Arg-Ser-
─────────────────────────────────────────────────┤ ├──
───RE5──────────────────────────────────────────────┤

50      52
Lys-Ile-Ser-Pro-Gln-Gly-Tyr-NH2
──────RE6──────────────┤

Fig.2

```
              1           10              20              30             40           50
Adrenomedullin  YRQSMNNFQGLRSFGCRFGTCTVQKLAHQIYQFTDKDKDNVAPRSKISPQGY-NH2
                                *              **               *   *     *        *
              ┌────┐
CGRP          ACDTATCVTHRLAGLLSRSGGVVKNNFVPTNVGSKA-F-NH2
              └────┘
                *            **              *  *   *        *

┌────┐
CGRP II       ACNTATCVTHRLAGLLSRSGGMVKSNFVPTNVGSKA-F-NH2
              └────┘
                *            **              *  *   *        *

┌────┐
Amylin        KCNTATCATQRLANFLVHSSNNFGAILSSTNVGSNT-Y-NH2
              └────┘
                *            **             *        *
```

DNA ENCODING ADRENOMEDULLIN

This is a division, of application Ser. No. 08/233,389, filed Apr. 26, 1994 now U.S. Pat. No. 5,639,855 entitled ADRENOMEDULLIN

BACKGROUND OF THE INVENTION

1. Field of the Invention

The present invention relates to adrenomedullin which is a novel peptide having a hypotensive effect, and proadrenomedullin N-terminal 20 peptide (hereinafter referred to as the "proAM-N20") having a catecholamine secretion inhibitory effect and proadrenomedullin N-terminal 10–20 peptide (hereinafter referred to as the "proAM-N(10–20)") having a sodium channel inhibitory effect, both of the proadrenomedullin N-terminal peptides being part of a pro-protein of adrenomedullin. More particularly, the present invention relates to adrenomedullin which can be purified from human phenochromocytoma (hereinafter referred to as "human PC"); structural genes of adrenomedullin, proAM-N20 and proAM-N(10–20); adrenomedullin and its proproteins encoded by the structural genes; expression vectors having the structural genes; transformants having the expression vectors; production methods for adrenomedullin, proAM-N20 and proAM-N(10–20) by using the transformants; an antibody against adrenomedullin or proAM-N20; an assay for quantifying adrenomedullin or proAM-N20 in a sample by using the antibody; and peptides useful in the preparation of the antibody and in the assay.

2. Description of the Related Art

Mammalian circulation is regulated by subtle mechanisms involving several neural and hormonal factors. Vasoactive peptides such as brain natriuretic polypeptide (BNP), a trial natriuretic polypeptide (ANP) and endothelin are known as important regulators in the cardiovascular system. It is assumed that BNP and ANP participate in blood pressure regulation and electrolyte metabolism regulation.

In order to clarify the intricacies of circulation, it is important that still unidentified vasoactive peptides be discovered. Especially, hypotensive peptides are desired which are useful in diagnosis and treatment of hypertensive hypercardia and cardiac failure.

SUMMARY OF THE INVENTION

The peptide of this invention comprises an amino acid sequence from Ser in the 13 position to Tyr in the 52 position of SEQ ID No. 1 and has a hypotensive effect.

In one embodiment, the peptide comprises an amino acid sequence from Tyr in the 1 position to Tyr in the 52 position of SEQ ID No. 1.

In one embodiment, the peptide comprises an amino acid sequence from Ala in the −73 position to Tyr in the 52 position of SEQ ID No. 1.

In one embodiment, the peptide consists of an amino acid sequence from Ser in the 13 position to Tyr in the 52 position of SEQ ID No. 1.

In one embodiment, the peptide consists of an amino acid sequence from Tyr in the 1 position to Tyr in the 52 position of SEQ ID No. 1.

In one embodiment, the peptide consists of an amino acid sequence from Ala in the −73 position to Tyr in the 52 position of SEQ ID No. 1.

In one embodiment, the carboxyl terminus of the peptide is amidated.

In one embodiment, Gly is attached to the carboxyl terminus of the peptide.

In one embodiment, the peptide comprises an amino acid sequence from Met in the −94 position to Leu in the 91 position of SEQ ID No. 1. In this amino acid sequence, the sequence from Met in the −94 position to Thr in the −74 position seems to be a signal peptide.

In one embodiment, Cys in the 16 position and Cys in the 21 position of SEQ ID No. 1 are linked by a disulfide bond.

In one embodiment, the disulfide bond which is linked between Cys in the 16 position and Cys in the 21 position of SEQ ID No. 1 is substituted with a —CH$_2$—CH$_2$— bond.

Alternatively, the peptide of the present invention comprises an amino acid sequence from Gln in the 3 position to Arg in the 12 position of SEQ ID No. 1, and generates an antibody for recognizing an amino acid sequence from Tyr in the 1 position to Tyr in the 52 position of SEQ ID No. 1. Examples of such a peptide include a peptide consisting of an amino acid sequence from Gln in the 3 position to Arg in the 12 position, and a peptide consisting of an amino acid sequence from Tyr in the 1 position to Arg in the 12 position of SEQ ID No. 1. Such a peptide corresponds to the N-terminal sequence of mature adrenomedullin and is useful in the preparation of an antibody and in an assay using the antibody.

Alternatively, the peptide of the present invention comprises an amino acid sequence from Ile in the 47 position to Tyr in the 52 position of SEQ ID No. 1, and generates an antibody for recognizing an amino acid sequence from Ser in the 13 position to Tyr in the 52 position of SEQ ID No. 1. Examples of such a peptide include a peptide consisting of an amino acid sequence from Ile in the 47 position to Tyr in the 52 position of SEQ ID No. 1, a peptide consisting of an amino acid sequence from Ser in the 45 position to Tyr in the 52 position of SEQ ID No. 1, and a peptide consisting of an amino acid sequence from Asn in the 40 position to Tyr in the 52 position of SEQ ID No. 1. Such a peptide corresponds to the C-terminal sequence of mature adrenomedullin and is useful in the preparation of an antibody and in an assay using the antibody.

In one embodiment, the carboxyl terminus of the peptide corresponding to the C-terminal sequence of mature adrenomedullin is amidated.

Still another peptide (proAM-N(10–20)) of the present invention comprises an amino acid sequence from Arg in the −64 position to Arg in the −54 position of SEQ ID No. 1 and has a sodium channel inhibitory effect. An example of such a peptide includes a peptide (proAM-N20) comprising an amino acid sequence from Ala in the −73 position to Arg in the −54 position of SEQ ID No. 1 and having also a catecholamine secretion inhibitory effect. Such a peptide corresponds to the N-terminal sequence of proadrenomedullin.

In one embodiment, the carboxyl terminus of the N-terminal peptide of proadrenomedullin is amidated.

In one embodiment, Gly is attached to the carboxyl terminus of the N-terminal peptide of proadrenomedullin.

Alternatively, the peptide of the present invention comprises an amino acid sequence from Trp in the −61 position to Arg in the −54 position of SEQ ID No. 1, and generates an antibody recognizing an amino acid sequence from Ala in the −73 position to Arg in the −54 position of SEQ ID No. 1. Examples of such a peptide include a peptide consisting of an amino acid sequence from Trp in the −61 position to Arg in the −54 position of SEQ ID No. 1 and a peptide consisting of an amino acid sequence from Phe in the −65 position to Arg in the −54 position of SEQ ID No. 1. Such a peptide corresponds to the C-terminal sequence of proAM-N20 and is useful in the preparation of an antibody and in an assay using the antibody.

In one embodiment, the carboxyl terminus of the peptide corresponding to the C-terminal sequence of proAM-N20 is amidated.

Alternatively, at least one of the amino acid sequences forming the peptide of the present invention can be labeled.

Alternatively, the peptide of the present invention further comprises Tyr labeled with a radioactive isotope which is attached to any of the above-mentioned peptides.

The DNA sequence of the present invention encodes any of the above-mentioned peptides.

In one embodiment, the DNA sequence comprises a base sequence from A in the 483 position to C in the 602 position of SEQ ID No. 2.

In one embodiment, the DNA sequence comprises a base sequence from A in the 483 position to C in the 605 position of SEQ ID No. 2.

In one embodiment, the DNA sequence comprises a base sequence from T in the 447 position to C in the 602 position of SEQ ID No. 2.

In one embodiment, the DNA sequence comprises a base sequence from T in the 447 position to C in the 605 position of SEQ ID No. 2.

In one embodiment, the DNA sequence comprises a base sequence from G in the 228 position to C in the 602 position of SEQ ID No. 2.

In one embodiment, the DNA sequence comprises a base sequence from G in the 228 position to C in the 605 position of SEQ ID No. 2.

In one embodiment, the DNA sequence comprises a base sequence from A in the 165 position to T in the 719 position of SEQ ID No. 2.

In one embodiment, the DNA sequence comprises a base sequence from C in the 255 position to T in the 287 position of SEQ ID No. 2.

In one embodiment, the DNA sequence comprises a base sequence from C in the 255 position to G in the 290 position of SEQ ID No. 2.

In one embodiment, the DNA sequence comprises a base sequence from G in the 228 position to T in the 287 position of SEQ ID No. 2.

In one embodiment, the DNA sequence comprises a base sequence from G in the 228 position to G in the 290 position of SEQ ID No. 2.

In one embodiment, the DNA sequence comprises a base sequence from T in the 264 position to T in the 287 position of SEQ ID No. 2.

In one embodiment, the DNA sequence comprises a base sequence from T in the 252 position to T in the 287 position of SEQ ID No. 2.

The expression vector of the present invention has any of the above-mentioned DNA sequences.

The transformant of the present invention is obtained by introducing the expression vector into a host.

The production method for a peptide of the present invention comprises the steps of: culturing the transformant in a medium; and collecting the generated peptide from the medium.

In one embodiment, the production method further comprises the step of amidating the carboxyl terminus of the collected peptide.

The antibody of the present invention recognizes any of the above-mentioned peptides.

In one embodiment, the antibody recognizes an amino acid sequence from Tyr in the 1 position to Arg in the 12 position of SEQ ID No. 1 or a portion included in the amino acid sequence.

In one embodiment, the antibody recognizes an amino acid sequence from Gln in the 3 position to Arg in the 12 position of SEQ ID No. 1 or a portion included in the amino acid sequence.

In one embodiment, the antibody recognizes an amino acid sequence from Ile in the 47 position to Tyr in the 52 position of SEQ ID No. 1 or a portion included in the amino acid sequence.

In one embodiment, the antibody recognizes an amino acid sequence from Ser in the 45 position to Tyr in the 52 position of SEQ ID No. 1 or a portion included in the amino acid sequence.

In one embodiment, the antibody recognizes an amino acid sequence from Asn in the 40 position to Tyr in the 52 position of SEQ ID No. 1 or a portion included in the amino acid sequence.

In one embodiment, the antibody recognizes an amino acid sequence from Trp in the −61 position to Arg in the −54 position of SEQ ID No. 1 or a portion included in the amino acid sequence.

In one embodiment, the antibody recognizes an amino acid sequence from Phe in the −65 position to Arg in the −54 position of SEQ ID No. 1 or a portion included in the amino acid sequence.

In one embodiment, the antibody recognizes an amino acid sequence in which the carboxyl group at the carboxyl terminus thereof is amidated or a portion included in the amino acid sequence.

In one embodiment, the antibody is a polyclonal antibody or a monoclonal antibody.

The immunological assay for a peptide of the present invention comprises the steps of: incubating a sample including any of the above-mentioned peptides with any of the above-mentioned antibodies under conditions for forming an antigen-antibody complex; and quantifying the antigen-antibody complex.

The vasorelaxant, the vasodilator or the medicament for cardiac failure of the present invention include any of the above-mentioned peptides as an effective component.

The kit for an immunological assay of the peptide of the present invention includes any of the above-mentioned antibodies.

In one embodiment, the kit includes any of the above-mentioned peptides.

Thus, the invention described herein makes possible the advantages of (1) providing adrenomedulluin, which is a novel peptide having a hypotensive effect, and a vasorelaxant and a vasodilator including adrenomedullin; (2) providing proAM-N20, which is a novel peptide having a catecholamine secretion inhibitory effect, and a catecholamine inhibitor including proAM-N20; (3) providing proAM-N (10–20) having a sodium channel inhibitory effect and a sodium channel inhibitor including proAM-N(10–20); (4) providing a vasorelaxant, catecholamine inhibitor and sodium channel inhibitor useful for the treatment of circulatory diseases such as cardiac failure, cardiac infarction and hypertension; (5) providing a DNA sequence encoding adrenomedullin and its precursor; (6) providing an expression vector having the DNA sequence; (7) providing a transformant having the expression vector; (8) providing a production method for adrenomedullin by using the transformant, capable of, if required, mass-producing adrenomedullin at low cost; (9) providing an antibody against adrenomedullin or proAM-N20; (10) providing a quantifying assay for adrenomedullin in a sample by using the antibody, which can be used for the diagnosis, the prevention and the treatment of circulatory diseases such as hypertension; (11) providing peptides useful in the preparation of the antibody and in the assay; and (12) providing a quantifying assay for adrenomedullin or proAM-N20 which can be used as a tumor marker.

These and other advantages of the present invention will become apparent to those skilled in the art upon reading and understanding the following detailed description with reference to the accompanying figures.

BRIEF DESCRIPTION OF THE DRAWINGS

FIG. 1 shows the amino acid sequence of adrenomedullin from Tyr in the 1 position to Tyr in the 52 position of SEQ ID NO: 1 which is derived from human PC of the present invention. Fragments RE1 through RE6 indicate fragments obtained by cleavage with arginylendopeptidase.

FIG. 2 shows a comparison between amino acid sequences of adrenomedullin derived from human PC of the present invention, (from Tyr in the 1 position to Tyr in the 52 position of SEQ ID NO: 1) calcitonin gene related peptide CGRP (SEQ ID NO:8), CGRP II SEQ ID NO:9), and amylin (SEQ ID NO:10).

DESCRIPTION OF THE PREFERRED EMBODIMENTS

Figure 3A:
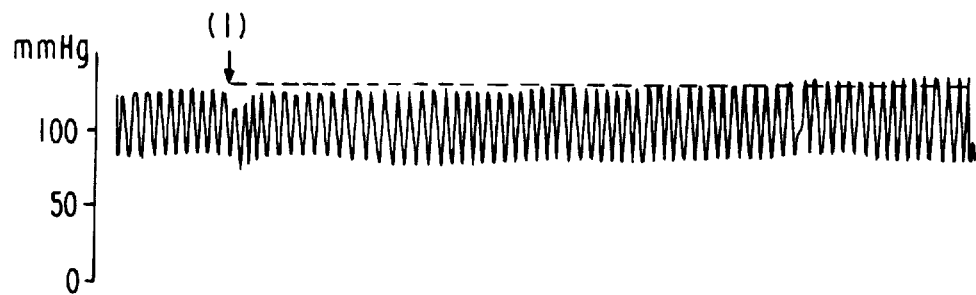
FIGS. 3A to 3D show variations in the blood pressure of anesthetized rats caused by a single intravenous administration of adrenomedullin of the present invention or CGRP.

The present inventors have made various studies to obtain hypotensive peptides. As a result, they have isolated a novel hypotensive peptide from human PC and clarified the primary structure and the immunological characteristics of the peptide to accomplish the present invention.

I. Definition:

Terms used herein to describe the present invention will be defined as follows:

"Adrenomedullin" is a novel hypotensive peptide. Especially, human-derived adrenomedullin provided by the present invention includes an amino acid sequence from Tyr in the 1 position to Tyr in the 52 position of SEQ ID No. 1 of the accompanying sequence listing. Porcine-derived adrenomedullin includes an amino acid sequence from Tyr in the 1 position to Tyr in the 52 position of SEQ ID No: 3 of the accompanying sequence listing. Adrenomedullin of the present invention, however, is not limited to these sequences, but includes any amino acid sequence including a conservative modification or defect which does not affect the activity thereof. The C-terminus of adrenomedullin can be amidated.

A peptide comprising an amino acid sequence from Met in the −94 position to Leu in the 91 position of SEQ ID No. 1 is assumed to be pre proadrenomedullin. A peptide, which is obtained by processing the signal peptide of the pre proadrenomedullin and comprises an amino acid sequence from Ala in the −73 position to Leu in the 91 position of SEQ ID No. 1, is assumed to be proadrenomedullin.

"Proadrenomedullin N-terminal 20 peptide (proAM-N20)" is a novel peptide having a catecholamine secretion inhibitory effect. Especially, human-derived proAM-N20 provided by the present invention consists of an amino acid sequence from Ala in the −73 position to Arg in the −54 position of SEQ ID No. 1. "Proadrenomedullin N-terminal 10–20 peptide (proAM-N(10–20))" is a novel peptide having a Na channel inhibitory effect. Especially, human-derived proAM-N(10–20) provided by the present invention consists of an amino acid sequence from Arg in the −64 position to Arg in the −54 position of SEQ ID No. 1. ProAM-N20 and proAM-N(10–20) of the present invention are not limited to these sequences, but include any amino acid sequence including a conservative modification or defect which does not affect the activity thereof. The C-termini of proAM-N20 and proAM-N(10–20) can be amidated.

"Amidation of the C-terminus" is one of the modifications of a peptide, in which a COOH group in the C-terminal amino acid of the peptide is changed to $CONH_2$. Some of the biologically active peptides functioning in an organism are first biosynthesized as a precursor protein having a larger molecular weight. The precursor protein is then matured by modification such as the amidation of the C-terminus. The amidation is conducted by a C-terminal amidating enzyme working on the precursor protein. The precursor protein always includes a Gly residue on the C-terminal side of the residue to be amidated, which is frequently followed by a basic amino acid sequence pair such as Lys-Arg and Arg-Arg on the C-terminal side (Mizuno, Seikagaku, Vol. 61, No. 12, pp. 1435–1461 (1989)).

An ordinary peptide having COOH at the C-terminus and a C-terminal amidated peptide are herein referred to as a peptide [X-Y] and a peptide $[X-Y]NH_2$, respectively, wherein X and Y indicate the positions of amino acids at the beginning and the end of the peptides in the accompanying sequence listing.

A peptide is "immunologically reactive" with an antibody when a specific epitope in the peptide is recognized by the antibody, thereby binding to the antibody. Several methods for determining whether or not a peptide is immunologically reactive with an antibody are known in the art. Enzyme-linked immunosorbent assay (ELISA) and radioimmunoassay (RIA) are especially preferred.

II. Methods to be used in the present invention:

In the present invention, isolation and analytical methods of a protein, a recombinant DNA technology and other immunological methods, all of which are known in the art, are used, except otherwise mentioned.

Typical methods which can be used in the present invention are as follows:

(1) Purification and structural analysis of adrenomedullin:

The derivation of adrenomedullin of the present invention is not particularly restricted. It can be derived from human PC or porcine adrenal medulla.

A crude extract from human PC is purified by various types of chromatography to obtain adrenomedullin. A fraction including the desired adrenomedullin can be obtained by monitoring the activity elevation of platelet cAMP.

An assay by monitoring the activity elevation of platelet cAMP has been used to isolate, from human PC, biologically active peptides such as vasoactive intestinal polypeptide (VIP) and calcitonin gene related peptide (CGRP) (Kitamura et al., Biochem. Biophys. Res. Commun., 185, 134–141 (1992)). These peptides are known to have a potent vasorelaxing effect, and are considered to bind to a specific receptor on the platelet membrane to increase the intracellular cAMP level. This assay is regarded to be a good means to study biologically active peptides. Therefore, the present inventors adopted this assay because it seemed to be a promising method to detect a vasoactive peptide in an extract from human PC tissues.

Structural analysis of adrenomedullin purified as mentioned above is performed by using, for example, a gas phase sequencer and the like.

(2) Confirmation of the hypotensive effect of adrenomedullin:

The hypotensive effect of adrenomedullin prepared as mentioned above can be confirmed, for example, in the same manner as reported with regard to rat brain natriuretic polypeptide (Kita et al., Eur. J. Pharmacol., 202, 73–79 (1991)). Specifically, an experimental animal such as a rat is anesthetized, and dosed with adrenomedullin by an appropriate method. Then, the blood pressure of the animal is continuously monitored through a right carotid artery catheter connected to a pressure transducer. The blood pressures before and after administration of adrenomedullin are compared to confirm the hypotensive effect of adrenomedullin.

(3) Cloning and sequencing of adrenomedullin cDNA:

A cloning and sequencing method for a DNA fragment including DNA encoding adrenomedullin of the present invention will now be described. An example of the method for sequencing cDNA encoding adrenomedullin of the present invention is as follows: A cDNA library (described in detail below) is prepared from total RNA of human PC. The library is screened by using a probe, thereby obtaining a positive clone. The positive clone is then sequenced by the DNA sequencing method.

(A) Production of a DNA probe:

The cDNA encoding adrenomedullin can be prepared, for example, from human PC as described above. A probe for cloning the adrenomedullin cDNA from a cDNA library derived from human PC is produced as follows:

A probe can be directly or indirectly produced based upon the peptide sequence at the amino terminus of adrenomedullin prepared as described in the above-mentioned item (1).

In the indirect production, a DNA primer for a polymerase chain reaction (PCR) is synthesized, for example, based on the amino acid sequence at the amino terminus. The DNA primer can be used to amplify a template for PCR prepared as below to obtain a probe for screening. For the preparation of such a template for PCR, cDNA obtained from human PC, where abundant adrenomedullin is considered to exist, can be used. Such cDNA can be prepared as follows. RNA is extracted from human PC by the guanidine thiocyanate method (Chomczynski, P. et al., Anal. Biochem., 162, 156–159 (1987)). A primer is annealed with the extracted RNA, and then DNA is synthesized from the primer by using reverse transcriptase to provide the desired cDNA.

Alternatively, such a probe can be prepared from DNA encoding adrenomedullin derived from another nonhuman animal. A method for screening for DNA encoding human-derived adrenomedullin using such a porcine derived probe found by the present inventors will be described in detail in the under mentioned examples.

The probe obtained as above is labeled to be used in subsequent screening.

(B) Screening of the library:

The cDNA library is produced from human PC tissues by a method known in the art. The preparation method for the cDNA library is described by, for example, Hyunh, V. T. et al., DNA Cloning Techniques—A Practical Approach (IRL Press, Oxford, 1984) and Okayama and Berg, Mol. Cell Biol. (1983) 3: 280–289.

The cDNA library is screened by using the probe prepared as described in item (A) under appropriate conditions to obtain a positive clone including cDNA encoding the desired adrenomedullin.

(C) Sequencing of cDNA:

The insert of the desired recombinant plasmid, i.e., the positive clone, obtained in the item (B) can be sequenced as follows. The insert is cleaved at a restriction enzyme recognition site present therein. Each of the cleaved DNA fragments is subcloned into an appropriate sequence vector, for example, BlueScript. Then, the base sequence of the cloned fragment is determined by using, for example, an automated DNA sequencer by the dye primer cycle sequencing method or the dideoxy cycle sequencing method. Thus, the base sequence of the entire fragment is determined.

(4) Production of adrenomedullin, its precursor protein, proAM-N20, its fragment for preparing an antibody and proAM-N(10–20):

Adrenomedullin, its precursor protein, proAM-N20, its fragment for preparing an antibody and proAM-N(10–20) can be produced by various methods including recombinant technology and the chemical synthesizing method. In the recombinant technology, DNA sequences encoding adrenomedullin, its precursor protein, proAM-N20, its fragment and proAM-N(10–20) are expressed by using various recombinant systems. An expression vector is constructed and a transformant having an appropriate DNA sequence is produced by known methods in the art. Expression can be conducted in a procaryote or an eucaryote.

Examples of a procaryote host include E.coli, Bacillus and other bacteria. When such procaryote is a host, a plasmid vector having a replication site and a control sequence compatible with the host is used. For example, E.coli is typically transformed with a derivative of pBR322, which is a plasmid derived from E.coli. The control sequence herein includes a promoter for initiation of transcription, an operator if necessary, and a ribosome binding site. Such a control sequence includes generally used promoters such as β-lactamase and lactose promoters (Chang et al., Nature, (1977) 198, 1056), tryptophan promoters (Goeddel et al., Nucleic Acids Res., (1980) 8, 4057), and $P_L$ promoters derived from λ phage and N-gene ribosome binding sites (Shimatake, Nature, (1981) 292, 128).

An example of an eucaryote host includes yeast. When such eucaryote is a host, a plasmid vector having a replication site and a control sequence compatible with the host is used. For example, yeast is transformed with pYEUra3 (Clontech). The other useful promoters in a yeast host include, for example, promoters for synthesizing a glycolytic enzyme such as a promoter for synthesizing 3-phosphoglycerate kinase (Hitzeman et al., J. Biol. Chem. (1980) 255, 2073). Further, promoters derived from an enolase gene or those derived from a Leu2 gene obtained from YEpl3 can be used.

Examples of an appropriate mammalian promoter include metallothionein, an early or late promoter derived from SV40, and other virus promoters such as those derived from polyoma virus, adenovirus II, bovine papilloma virus and avian sarcoma virus.

A transformant can be obtained by introducing an expression vector into appropriate host cells. A desired peptide such as adrenomedullin, its precursor protein, proAM-N20, its fragment and proAM-N(10–20) can be obtained by culturing the transformant under appropriate conditions.

A C-terminal amidated peptide is prepared by one of the following. A carboxyl group at the C-terminus of a peptide obtained by an expression in a host is chemically amidated;

or a peptide is first prepared so as to have Gly attached to the C-terminus of the desired peptide, and is then allowed to react with the above-mentioned C-terminal amidating enzyme for amidation.

The above-mentioned peptides, such as adrenomedullin, can be chemically synthesized by a method known in the art. For example, they can be synthesized by the solid phase method by using a peptide synthesizer. The C-terminal amidated peptide can be synthesized by using a peptide synthesizer as follows. First, an amino acid corresponding to a C-terminal amino acid is bound to a benzhydryl amine resin. Then, a condensation reaction is performed by binding to the N-terminus of the bound amino acid under standard condensation conditions using DCC/HOBt. This condensation reaction is repeated so as to obtain the desired amino acid sequence. The desired peptide is cut out from the resultant peptide resin by a general cleavage method (trifluoromethanesulfonic acid method).

A disulfide bond can be linked, for example, by oxidizing the peptide with air or another appropriate oxidant. The disulfide bond can be substituted with a —$CH_2$—$CH_2$— bond by a known method (O. Keller et al., Helv. Chim. Acta (1974) 57:1253). Generally, cleavage in the disulfide bond can be avoided by substituting the disulfide bond with a —$CH_2$—$CH_2$— bond, resulting in obtaining a stable protein.

(5) Labeling of adrenomedullin, its precursor protein, proAM-N20, its fragment for preparing an antibody, and proAM-N(10–20):

The adrenomedullin, its precursor protein, proAM-N20, its fragment for preparing an antibody, and proAM-N (10–20) can be labeled with a radioactive isotope, an enzyme, a fluorescent material, or the like. These labelings can be conducted by methods known to those skilled in the art.

Examples of the radioactive isotope to be used for labeling include $^{14}C$, $^{3}H$, $^{32}P$, $^{125}I$, and $^{131}I$, among which $^{125}I$ is preferred. These radioactive isotopes can be labeled to the peptide by a chloramine T method, a peroxidase method, an iodogen method, a Bolton-Hunter method, or the like.

Examples of the enzyme to be used for labeling include horseradish peroxidase, bovine mucosa alkaline phosphatase, and E. coli β-galactosidase.

Examples of the fluorescent material to be used for labeling include fluorescamine, fluorescein, fluoresceinisothiocyanate, and tetramethylrhodamine isothiocyanate.

The labeled peptide is useful as a tracer or for an immunological assay described below.

(6) Immunological assay for adrenomedullin, its fragment, and proAM-N20:

The immunological assay in the present invention can be used for quantifying an antigen in a sample. Examples of the immunological assay include a method in which an antigen labeled with a radioactive isotope, an enzyme, or a fluorescent material and an unlabeled antigen are competitively reacted with an antibody. An immunoassay with two antibodies and a sandwich techniques can also be used: In the immunoassay with two antibodies, an antigen is immobilized on a solid phase such as a microplate or a plastic cup, incubated with a diluted antiserum or a purified antibody, and further incubated with an antiimmunoglobulin labeled with a radioactive isotope, an enzyme, or a fluorescent material, thereby obtaining a labeled binding substance. In the sandwich technique, an antibody is immobilized on a solid phase, incubated with an antigen, and further incubated with an antibody labeled with a radioactive isotope, an enzyme, or a fluorescent material, thereby obtaining a labeled binding substance. Examples of the radioactive isotope to be used for labeling include $^{32}P$, $^{3}H$, $^{14}C$, $^{125}I$, and $^{131}I$ among which $^{125}I$ is preferred. The enzyme to be used for labeling is preferably horseradish peroxidase, bovine mucosa alkaline phosphatase, and E. coli β-galactosidase. Among them, horseradish peroxidase is preferably used. Examples of the fluorescent material to be used for labeling include fluoresceinisothiocyanate and tetramethylrhodamine isothiocyanate. However, the radioactive isotope, the enzyme, and the fluorescent material are not limited to those described herein.

Specifically, a peptide such as adrenomedullin, proAM-N20, or its fragment is used as an immunogen. Such as immunogen includes: a peptide comprising an amino acid sequence, for example, from Gln in the 3 position to Arg in the 12 position, from Tyr in the 1 position to Arg in the 12 position, from Ile in the 47 position to Tyr in the 52 position, from Ser in the 45 position to Tyr in the 52 position, or from Asn in the 40 position to Tyr in the 52 position of SEQ ID No. 1; a peptide which includes any of the above-mentioned amino acid sequences and can generate an antibody for recognizing adrenomedullin; a peptide comprising an amino acid sequence from Trp in the –61 position to Arg in the –54 position or from Phe in the –65 position to Arg in the –54 position of SEQ ID No. 1; a peptide which includes any of these amino acid sequences and can generate an antibody for recognizing proAM-N20; and any of these peptides combined with bovine thyroglobulin and the like. By using such an immunogen, an animal such as a mouse, a rat, a rabbit, a fowl, and a goat is immunized to prepare an antibody derived from the serum of the animal. Alternatively, a cell from the spleen of the animal is fused with a cell such as a myeloma cell to produce a hybridoma, from which a monoclonal antibody is produced.

Next, a known concentration of an unlabeled antigen and a polyclonal or monoclonal antibody derived from the serum are added to a predetermined amount of a labeled peptide including the same kind of antigen as that used in the immunization, thereby causing an antigen-antibody competitive reaction. The labeled antigen bound to the antibody is separated from the labeled antigen not bound to the antibody by an appropriate method. The radioactivity or the enzyme activity of the labeled antigen bound to the antibody is then measured. This procedure is repeated with various concentrations of the unlabeled antigen. As the concentration of the unlabeled antigen is increased, the amount of the labeled antigen bound to the antibody is decreased. The relationship between them is plotted into a graph to obtain a standard curve.

Then, a sample including an unknown concentration of the antigen is added to the above-mentioned reaction system instead of the unlabeled antigen in a known concentration. After the competitive reaction, the radioactivity, the enzyme activity or the fluorescence intensity of the antigen bound to the antibody is measured. The result of the measurement is applied to the standard curve to determine the concentration of the antigen in the sample.

When the sandwich techniques is used, two kinds of antibodies against different epitopes of adrenomedullin are first prepared. One antibody is labeled with a radioactive isotope, an enzyme, or a fluorescent material and the other antibody is allowed to bind to a solid phase as a solid phase antibody or is made to be able to specifically bind to a solid phase. These antibodies are allowed to react with antigens in various concentrations to form a plurality of antigen-antibody complexes. Since the antigen-antibody complexes are bound to solid phases, the solid phases are separated from the complexes, and the radio-activity, the enzyme activity or the fluorescence intensity in the solid phases is measured. The relationship between the radioactivity, the enzyme activity or the fluorescence intensity and the concentration of the antigen is plotted to obtain a standard curve.

When a sample including an unknown concentration of antigen is added to the reaction system, the concentration of the antigen can be determined by applying the radioactivity or the enzyme activity measured after the reaction to the standard curve.

The antibody used in the assay in the present invention can be an antibody fragment used in a general immunological assay such as a Fab and a Fab'.

(7) Confirmation of the effect of proAM-N20 on catecholamine secretion:

The effect of proAM-N20 of the present invention on the secretion of catecholamine can be confirmed as follows. ProAM-N20 is added to cultured bovine adrenal medulla cells for incubation. The resultant is subjected to HPLC to measure the amount of catecholamine secreted therein. The same procedure is repeated with regard to a control including no proAM-N20. When the obtained results are compared, the effect of proAM-N20 can be confirmed.

(8) Confirmation of the effect of proAM-N(10–20) on sodium channel:

The effect of proAM-N(10–20) of the present invention on the sodium channel can be confirmed as follows. After treating cultured bovine adrenal medulla cells with proAM-N(10–20), the cells are stimulated with carbachol and the flow of $^{22}$Na into the cells is measured with HPLC. The same procedure is repeated with regard to cells which have not been treated with proAM-N(10–20). When the obtained results are compared, the effect of proAM-N(10–20) can be confirmed.

(9) Usage and administration of adrenomedullin, its precursor protein, proAM-N20 and proAM-N(10–20):

Adrenomedullin and its precursor protein of the present invention have a hypotensive effect and a vasodilating effect, and therefore, they are useful in the treatment of a disease such as hypertension and cardiac incompetence.

ProAM-N20 of the present invention has a catecholamine secretion inhibitory effect, and therefore, it is useful as a catecholamine inhibitor for the treatment of hypertension and the like.

ProAM-N(10–20) of the present invention has a sodium channel inhibitory effect, and therefore, it is useful as a sodium channel inhibitor for the treatment of hypertension and the like.

Adrenomedullin, its precursor protein, proAM-N20 and proAM-N(10–20) of the present invention can be administered in the same manner as used for a conventional peptide preparation described in Remington's Pharmaceutical Sciences, Mack Publishing, Eston, Pa. These peptides can be administered preferably by an injection, and more preferably by an intravenous injection. The dose level of adrenomedullin is approximately 0.1 nmol to 3.0 nmol per 1 kg of a patient.

Adrenomedullin, its precursor protein, proAM-N20 and proAM-N(10–20) of the present invention can be used as medicaments for an intravenous injection or drops for easing the load on the heart in order to improve cardiac incompetence and the like especially in the acute phase of cardiac infarction.

The peptides in which Gly is attached to the C-termini of adrenomedullin, its precursor protein, proAM-N20 and proAM-N(10–20) can be directly administered since the carboxyl group at the C-termini of these peptides is amidated in an organism due to the function of a C-terminal amidating enzyme in the organism on Gly as mentioned above.

Examples

The present invention will now be described by way of examples.

[Example 1]

(Purification of adrenomedullin from human PC)

Adrenomedullin was purified from human PC tissues resected at surgery from a norepinephrine dominant PC patient in the same manner as described by Kitamura et al., Biochem. Biophys. Res. Commun., 185, 134–141 (1992).

The purification was specifically performed as follows. The resected PC tissues were finely chopped, and boiled in a 4-fold volume of 1M acetic acid for 10 minutes, thereby inactivating the intrinsic protease. The resultant was cooled and homogenized with a polytron mixer at a temperature of 4° C. The homogenized suspension was centrifuged at 20,000×g for 30 minutes to provide a supernatant. The supernatant was subjected to acetone-sedimentation at a concentration of 66%. After removing the sediment, the remaining supernatant was condensed with a rotary evaporator. The resultant was diluted with water into a double volume and applied upon a C-18 silica gel column (270 ml, Chemco LS-SORB ODS). The materials adsorbed on the column were eluted with 60% $CH_3CN$ containing 0.1% trifluoroacetic acid (TFA). The eluate was evaporated and applied upon a SP-Sephadex C-25 column ($H^+$-form, 2×15 cm, Pharmacia) which had been equilibrated with 1M acetic acid. Successive elutions with 1M acetic acid, 2M pyridine and 2M pyridine-acetic acid (pH 5.0) result in three fractions designated as SP-I, SP-II and SP-III.

The SP-III fraction having more than 90% platelet cAMP elevation activity was separated by gel filtration on a Sephadex G-50 column. The activity assay was identical to the above-mentioned method described by Kitamura et al. Specifically, 25 μl of a sample dissolved in a suspension medium containing 135 mM NaCl, 2 mM EDTA, 5 mM glucose, 10 mM theophylline and 15 mM HEPES (pH 7.5) was incubated at a temperature of 37° C. for 10 minutes. Then, 25 μl of washed rat platelets ($4.0×10^5$) was added thereto to initiate the reaction, and the mixture was incubated for 30 minutes. To the resultant, 150 mM HCl was further added, and the mixture was heated for 3 minutes to stop the reaction. The resultant sample was concentrated with a speedvac concentrator and dissolved in 100 μl of a 50 mM sodium acetate buffer (pH 6.2). Cyclic AMP in the obtained solution was succinylated for analysis by cAMP RIA.

The fraction having the platelet cAMP elevation activity with a molecular weight of 4,000 to 6,000 was further separated by the CM ion exchange HPLC on a TSK CM-2SW column (8.0×300 mm, Tosoh). Adrenomedullin was finally purified by reverse phase HPLC on a phenyl column (4.6×250 mm, Vydac) and a μBondasphere C-18 column (4.6×150 mm, 300A, Waters).

(Structural analysis of adrenomedullin)

Two hundred pmol of purified adrenomedullin was reduced and S-carboxymethylated (RCM) by a method described by Kangawa et al., Biochem. Biophys. Res. Commun. 118, 131–139 (1984). The obtained RCM-adrenomedullin was purified by reverse phase HPLC. Half of the purified RCM-adrenomedullin (100 pmol) was subjected to a gas phase sequencer (Model, 470A/120A, Applied Biosystems). The remaining half of the purified RCM-adrenomedullin was digested with 400 ng of arginylendopeptidase (Takara Shuzo, Kyoto, Japan) in 50 μl of 50 mM Tris-HCl (pH 8.0) containing 0.01% Triton-X 100 at a temperature of 37° C. for 3 hours, thereby producing peptide fragments RE1 to RE6. These peptide fragments RE1 to RE6 were separated from one another by the reverse phase HPLC on a semi-micro column of Chemcosorb 3 ODS H (2.1×75 mm, Chemco, Osaka, Japan), and each of the obtained fragments was sequenced with a gas phase sequencer (Model 470A/120A, Applied Biosystems). to determine the entire amino acid sequence of adrenomedullin as shown in FIG. 1. Adrenomedullin consisted of 52 amino acids and had an intramolecular disulfide bond. Tyr at the C-terminus was found to be amidated because native adrenomedullin [45–52] (i.e., the fragment RE6) was eluted at the same position as synthetic adrenomedullin [45–52] $NH_2$ by reverse phase HPLC. In this manner, the structure of adrenomedullin was demonstrated by chromatographic comparison between native adrenomedullin and synthetic adrenomedullin prepared so as to correspond to the determined sequence of native adrenomedullin.

A computer search (PRF-SEQDB, Protein Research Foundation, Osaka, Japan) found no report on the same peptide sequence. Therefore, adrenomedullin was confirmed to be a novel peptide having a biological activity. The sequence homology of adrenomedullin to human CGRP (Morris et al., Nature, 308, 746–748 (1984)), CGRP II (Steenbergh et al., FEBS Lett., 183, 403–407 (1985)) and amylin (Cooper et al., Proc. Natl. Acad. Sci. U.S.A., 84, 8628–8632 (1987)) was as low as approximately 20% as shown in FIG. 2, although the six residue ring structure with an intracellular disulfide bond and the C-terminal amidated structure are common to them all. The 14 residue amino terminal extension present in adrenomedullin does not exist in CGRP and amylin.

[Example 2]
(Hypotensive effect of adrenomedullin)

Figure 3B:
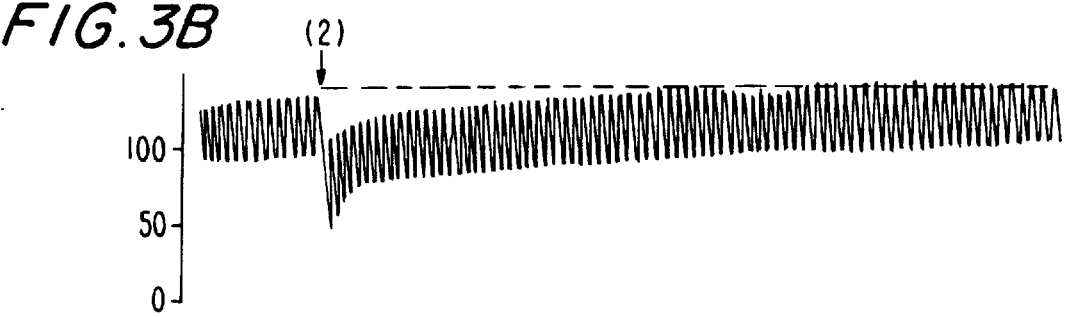
Figure 3C:
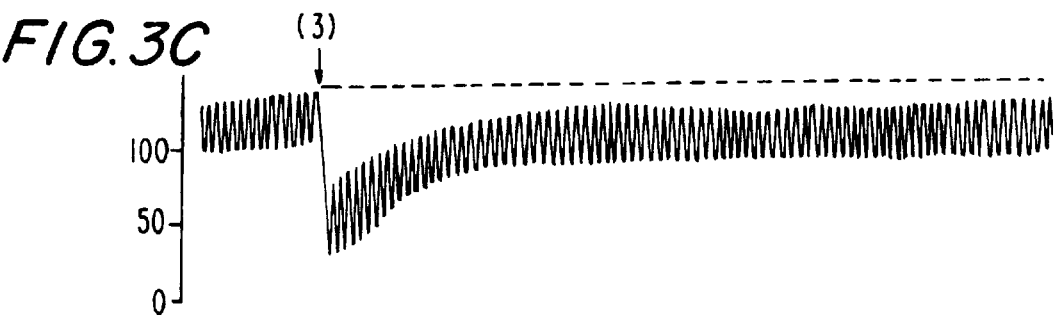
Figure 3D:
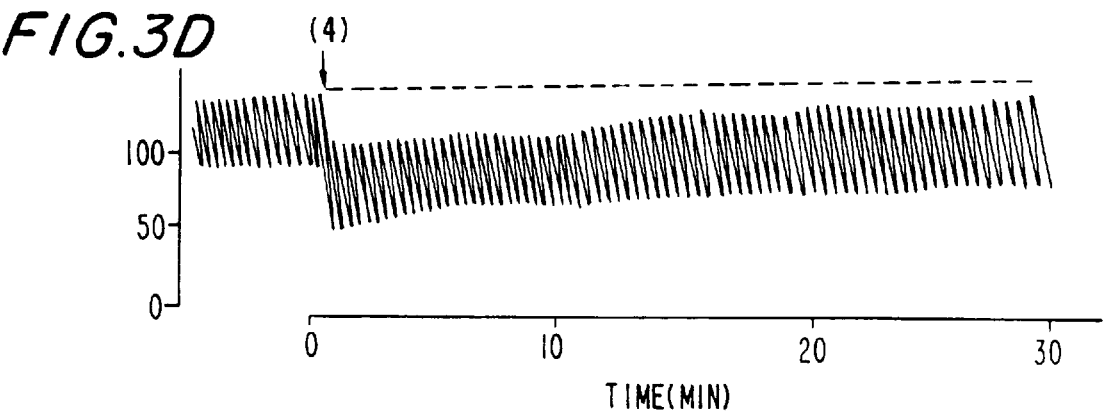

The hypotensive effect of adrenomedullin was tested by the same method as reported with regard to rat brain natriuretic polypeptide (Kita et al., Eur. J. Pharmacol., 202, 73–79 (1991)). Male Wistar rats (two weeks old, 300 g) were anesthetized by an intraperitoneal injection of pentobarbital sodium (50 mg/kg). The blood pressure of each rat was continuously monitored through a right caroid artery catheter (PE-50) connected to a Statham pressure transducer (Model P231D, Gould). A PE-10 catheter was inserted into the right jugular vein in order to administer a maintenance solution and a peptide. After equilibration for at least 60 minutes, either CGRP or adrenomedullin was intravenously injected to each rat. FIGS. 3A through 3D show the variation in the blood pressure of the rat monitored at the time of the injection of CGRP or adrenomedullin. FIGS. 3A, 3B and 3C indicate the variation caused by the injection of 0.3 nmol/kg, 1.0 nmol/kg and 3.0 nmol/kg of adrenomedullin, respectively, and FIG. 3D indicates the variation caused by the injection of 3.0 nmol/kg of CGRP. The injected adrenomedullin was a peptide consisting of the amino acids 1–52 of SEQ ID No. 1, the C-terminus of which was amidated.

A single intravenous injection of adrenomedullin caused a fast, potent and long lasting hypotensive effect in a dose dependent manner. When 3.0 nmol/kg of adrenomedullin was intravenously injected, the maximal decrease in the mean blood pressure was 53±5.0 mmHg (i.e., a mean±S.E.M., n=4). Such a significant hypotensive effect lasted for 30 to 60 minutes. As is apparent from FIGS. 3C and 3D, the hypotensive activity of adrenomedullin was comparable to that of CGRP, which has been reported as one of the strongest vasorelaxants. Accordingly, adrenomedullin was confirmed to have an effectively long lasting hypotensive effect.

Next, adrenomedullin consisting of the amino acids 13–52 of SEQ ID No. 1 and having the amidated C-terminus was administered to check the variation in the blood pressure of the rats.

The peptide [13–52]$NH_2$ was synthesized with a peptide synthesizer (Applied Biosystems, 430A) as follows. First, an amino acid corresponding to a C-terminal amino acid, i.e., Tyr in the 52 position, was bound to a benzhydryl amine resin. Then, a condensation reaction was performed by binding to the N-terminus of the bound amino acid (i.e., Tyr) under standard condensation conditions using DCC/HOBt. This condensation reaction was repeated so as to obtain the desired amino acid sequence. The desired peptide was cut out of the obtained peptide resin by the general cleavage method (trifluoromethanesulfonic acid method), oxidized with air or an appropriate oxidant such as potassium ferricyanide and iodine to form a disulfide bond therein, if necessary, and purified by reverse phase HPLC.

When the obtained peptide [13–52]$NH_2$ was administered in the same manner as above, it exhibited a comparable hypotensive effect.
(Check of heart rate upon administration of adrenomedullin)

Male Wistar rats each weighing 330 to 390 g were purchased from Charles River Inc. Each of the rats was anesthetized by an intraperitoneal injection of pentobarbital sodium (50 mg/kg). A polyethylene catheter (PE-250) was inserted into the trachea so as to aid breathing. Mean blood pressure (MBP) and heart rate (HR) were monitored through a right fermoral artery catheter (PE-50) connected to a Statham pressure transducer (Model P231D, Gould) and a polygraph (Model 141–6, San-Ei). A PE-10 catheter was inserted into the right atrium through the right jugular vein. A thermosensor was placed in the ascending aorta through the right carotid artery. Under these conditions, cardiac output was measured by the thermodilution method (Model 600, Cardiotherm). During the measurement, the rat was placed on a heat table so as to maintain the arterial temperature at 36° to 37° C.

Each rat was allowed to equilibrate for 45 minutes after the surgery. Then, human adrenomedullin (1.0 nmol/kg) dissolved in saline (n=8) or the same amount of isotonic saline (n=8) was intravenously injected to each rat. In the previously performed preliminary test, the vasodepressor response caused by this amount of adrenomedullin was approximately half of the maximal efficacy. The cardiac output was measured 15 minutes before, at the time of, and 2, 5, 10 and 30 minutes after the administration.

A cardiac index (CI), a stroke volume index (SVI) and a total peripheral resistance index (TPRI) were calculated by the following formulae:

CI (ml/min. per 100 g of body weight)=cardiac output/100 g of body weight

SVI (μl/beat per 100 g of body weight)=CI/HR

TPRI (u·100 g of body weight)=MBP/CI

The human adrenomedullin and peptide used in the above were synthesized by the solid phase method, and its homology was confirmed by reverse phase HPLC.

Figure 4:
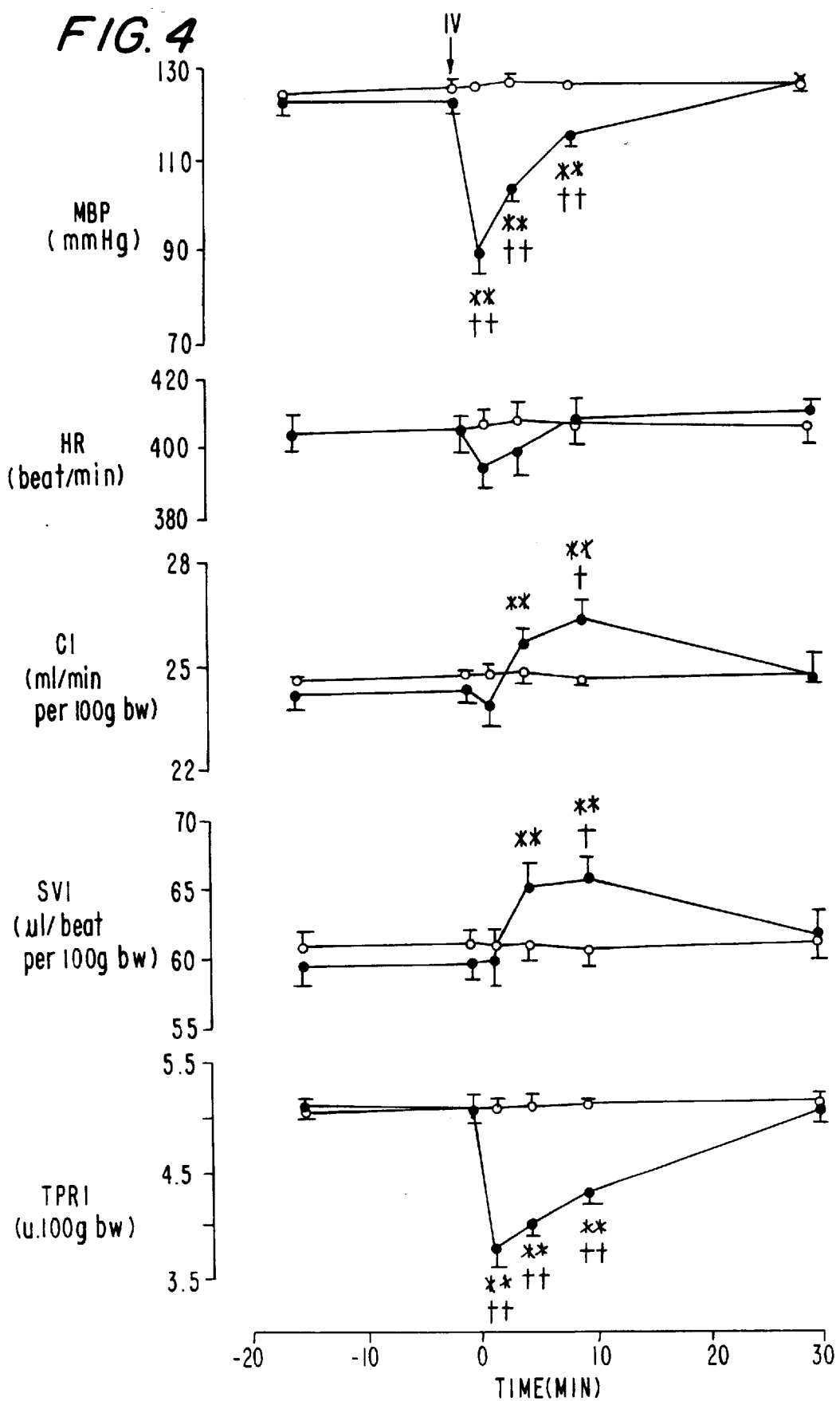
FIG. 4 shows variations of various hemodynamic parameters in anesthetized rats caused by a single intravenous administration of adrenomedullin of the present invention.

FIG. 4 indicates the change with time of MBP, HR, CI, SVI and TPRI when human adrenomedullin dissolved in saline (shown with closed circle) and saline alone (shown with open circle) were administered to the respective rats. Each value is indicated as a mean±S.E.M.

As shown in FIG. 4, MBP was significantly decreased 2, 5 and 10 minutes after the administration of human adrenomedullin, and returned to the initial level after 30 minutes. TPRI was significantly decreased also 2, 5 and 10 minutes after the administration with a decrease in MBP. To the contrary, CI and SVI were increased. HR was slightly decreased 2 minutes after the administration, but did not change significantly. With regard to the rats injected with saline, CI, SVI, TPRI, MBP and HR remained unchanged.

[Example 3]

(RIA utilizing adrenomedullin and its fragment)

(A) RIA utilizing an antibody against a peptide fragment comprising the N-terminal amino acid sequence of adrenomedullin:

A peptide [1–12] and a peptide [3–12] were synthesized by the solid phase method with a peptide synthesizer (Applied Biosystems, 430A) and purified by reverse phase HPLC.

Ten mg of the peptide [1–12] and 20 mg of bovine thyroglobulin were allowed to conjugate to each other in 2 ml of 0.1M sodium phosphate buffer (pH 7.4) by glutaraldehyde (Miyata et al., Biochem. Biophys. Res. Commun., 120, 1030–1036 (1984)). The obtained reaction mixture was dialyzed against 50 mM sodium phosphate buffer (pH 7.4)/0.08M NaCl, and the resultant was used for immunization as described in the above-mentioned paper by Miyata et al. The immunization was performed by using New Zealand white rabbits. The antiserum obtained from the immunized animals was used in the following RIA.

RIA for the peptides [1–12] and [3–12] were conducted in the same manner as reported with regard to β-neo-endorphin (Kimura et al., Biochem. Biophys. Res. Commun., 109, 966–974 (1982)).

Specifically, 100 µl of the peptide [1–12] or [3–12] in a known concentration, 50 µl of the antiserum obtained as above at a dilution of 1:6,000, and 50 µl of $^{125}$I-labeled ligand (18,000 cpm), which had been prepared by the lactoperoxidase method (Kitamura et al., Biochem. Biophys. Res. Commun., 161, 348–352 (1989)), were mixed to obtain an RIA reaction mixture. The mixture was incubated for 24 hours. Then, the labeled ligand which was bound to the antiserum (hereinafter referred to as the "bound ligand") was separated from the labeled ligand which was not bound to the antiserum (hereinafter referred to as the "unbound ligand") by the polyethylene glycol method. The radioactivity of the obtained pellet was counted with a gamma counter (ARC-600, Aloka), and the assay was performed in duplicate at a temperature of 4° C. By repeating the above procedure with regard to various concentrations of each peptide, a standard curve was obtained. The standard curves for the peptide [1–12] and the peptide [3–12] were identical to each other. Half maximal inhibition of radioiodinated ligand binding by the peptide [1–12] or [3–12] was observed at 10 fmol/tube.

Next, a sample solution including an unknown concentration of adrenomedullin was trypsinized in 100 µl of 0.1M NH$_4$HCO$_3$ containing 20 µg of bovine serum albumin (BSA) with 1 µg of trypsin (Worthington). A reaction mixture consisting of 100 µl of the resultant sample solution, 50 µl of the antiserum at a dilution of 1:6,000, and 50 µl of $^{125}$I-labeled ligand (18,000 cpm), which had been prepared by the lactoperoxidase method (Kitamura et al., Biochem. Biophys. Res. Commun., 161, 348–352 (1989)), was incubated for 24 hours. Then, the bound ligand was separated from the unbound ligand by the polyethylene glycol method. The radioactivity of the obtained pellet was counted with the gamma counter (ARC-600, Aloka), and the assay was performed in duplicate at a temperature of 4° C.

Through the above-described RIA, the antiserum was found to recognize a peptide, which was a fragment of adrenomedullin produced by digestion with trypsin. Therefore, the peptides [1–12] and [3–12] were found to be useful in the production of an antibody against adrenomedullin.

(B) RIA utilizing an antibody against a peptide fragment comprising the C-terminal amino acid sequence of adrenomedullin:

Peptide [1–52]NH$_2$, [13–52]NH$_2$, [40–52]NH$_2$, [45–52] NH$_2$ and [45–52], [47–52]NH$_2$ and [47–52], and [1–12] were synthesized by the solid phase method with a peptide synthesizer (Applied Biosystems, 430A) and purified by reverse phase HPLC. The C-terminal amidated peptides among the above were synthesized with a peptide synthesizer as follows. First, an amino acid corresponding to a C-terminal amino acid, i.e., Tyr in the 52 position, was bound to a benzhydryl amine resin. Then, a condensation reaction was performed by binding to the N-terminus of the bound amino acid (i.e., Tyr) under standard condensation conditions using DCC/HOBt. This condensation reaction was repeated so as to obtain the desired amino acid sequences. The desired peptides were respectively cut out of the obtained peptide resins by the general cleavage method (trifluoromethanesulfonic acid method).

A disulfide bond was formed as described above.

A mixture of 9.3 mg of the peptide [40–52]NH$_2$ and 10.3 mg of bovine thyroglobulin was dissolved in 0.5 ml of a saline. To the resultant solution was added 50 mg each of water soluble carbodiimide five times every two hours while stirring at room temperature. The resultant mixture was continuously stirred at a temperature of 4° C. overnight. Then, the mixture was dialyzed five times against 500 ml of a saline and twice against 500 ml of a sodium phosphate buffer. The obtained dialysate was adjusted to a final volume of 11 ml by adding a sodium phosphate buffer to provide an antigenic conjugate solution.

The antigenic conjugate solution (1.5 to 3 ml) was emulsified with an equal volume of complete Freund's adjuvant. A New Zealand white rabbit was immunized with the emulsified solution, and the antiserum obtained from the immunized animal was used in the following RIA.

RIA for the peptides [1–52]NH$_2$, [40–52]NH$_2$, [45–52] NH$_2$, [45–52], [47–52]NH$_2$, [47–52], [1–12], and CGRP, CGRP-II and amylin were conducted in the same manner as reported with regard to β-neo-endorphin by Kitamura et al., Biochem. Biophys. Res. Commun., 109, 966–974 (1982).

Specifically, a reaction mixture consisting of 100 µl of one of the peptides in a known concentration, 50 µl of the antiserum obtained in the abovementioned manner at a dilution of 1:180,000, and 50 µl of $^{125}$I-labeled ligand (18,000 cpm) prepared by the Bolton-Hunter method (A. E. Bolton and W. M. Hunter, Biochemical J. (1973) 133, 529–539) was incubated for 24 hours. Then, the bound ligand was separated from the unbound ligand by the polyethylene glycol method. The radioactivity of the obtained pellet was counted with a gamma counter (ARC-600, Aloka), and the assay was performed in duplicate at a temperature of 4° C.

A standard curve was plotted from the results. Half maximal inhibition of radioiodinated ligand binding to the peptides [13–52]NH$_2$, [40–52]NH$_2$, [45–52]NH$_2$ and [47–52]NH$_2$ by the peptide [1–52]NH$_2$ was observed at 11 fmol/tube.

The results of the above-mentioned RIA revealed that the antiserum had a reactivity against the peptide [40–52]NH$_2$ which is an antigen, a crossreactivity against the peptides

[1–52]NH$_2$, [45–52]NH$_2$ and [47–52]NH$_2$ and no crossreactivity against the peptides [45–52], [47–52] and [1–12], CGRP, CGRP-II and amylin.

(Distribution of adrenomedullin in each tissue)

From a human PC, an adrenal medulla, a lung, a kidney, a brain cortex, an intestine and a ventricle, 1.0 g of tissues were respectively taken out, and boiled in a 5-fold volume of water for 10 minutes to inactivate intrinsic protease. After cooling, glacial acetic acid was added to each so as to make the resultant mixture 1M. The mixture was homogenized with a polytron mixer at a temperature of 4° C. Then, the mixture was centrifuged at 24,000×g for 30 minutes, and the supernatant of the thus obtained extract was applied upon a Sep-Pak C-18 cartridge column (Waters), which had been previously equilibrated with a 1M acetic acid. The materials adsorbed on the column were eluted with 3 ml of 60% acetonitrile containing 0.1% TFA. Adrenomedullin in the resultant solution was analyzed by reverse phase HPLC on a TSK ODS 120A column (4.6×150 mm, Tosoh) under the conditions described by Ichiki et al., Biochem. Biophys. Res. Commun. 187, 1587–1593 (1992).

The presence of adrenomedullin in each of the above-mentioned human tissues was checked by RIA accompanied with identification of the peptide by reverse phase HPLC. The results are shown in Table 1 below.

TABLE 1

| Tissue | Immunoreactive adrenomedullin (fmol/mg wet tissue) |
| --- | --- |
| PC | 1,900 ± 450 |
| Adrenal medulla | 150 ± 24 |
| Lung | 1.2 ± 0.16 |
| Kidney | 0.15 ± 0.012 |
| Brain cortex | <0.1 |
| Intestine | <0.1 |
| Ventricle | <0.1 |

As shown in Table 1, human PC was found to include abundant adrenomedullin in an amount of 1,900±450 fmol/mg wet tissue. Adrenomedullin was present in a normal adrenal medulla in a large amount of 150±24 fmol/mg wet tissue. The concentration of adrenomedullin in a lung or a kidney was less than 1% of that in a normal adrenal medulla. However, the total amount of adrenomedullin in the lung and the kidney was larger than the amount in an adrenal medulla. Although CGRP, which works as a neuropeptide, exists in brain and peripheral nerves, adrenomedullin was not detected in the brain. Further, the previously performed preliminary experiment showed that adrenomedullin existed in healthy human plasma at a considerable concentration (19±5.4 fmol/ml, n=4). Therefore, adrenomedullin generated in peripheral tissues, the adrenal medulla, the lung and the kidney works as a circulating hormone participating in blood pressure control. Further, enhanced production of adrenomedullin in human PC is considered relevant to various symptoms in PC patients such as orthostatic hypotension.

[Example 4]

(Purification and structural analysis of adrenomedullin from the porcine adrenal medulla)

(A) Purification of adrenomedullin from the porcine adrenal medulla:

Porcine adrenomedullin was purified from the porcine adrenal medulla by the same purification method as that used for human adrenomedullin in Example 1.

Specifically, the porcine adrenal medulla was finely chopped, boiled in a 10-fold volume of 1M acetic acid for 10 minutes to inactivate intrinsic protease. The resultant mixture was cooled, and homogenized with a polytron mixer at a temperature of 4° C. The obtained suspension was centrifuged at 22,000×g for 30 minutes. The supernatant of the thus obtained extract was applied upon a Sep-Pak C-18 cartridge column (20 ml, Waters). The materials adsorbed on the column were eluted with 60% CH$_3$CN containing 0.1% TFA. The obtained eluate was evaporated. The resultant solution was used as a crude peptide extract in the succeeding RIA conducted as in Example 3. As described in Example 3, this RIA has been established as an RIA system utilizing a peptide [1–12] derived from human adrenomedullin.

The crude peptide extract was separated by gel filtration chromatography (Sephadex G-50, Fine, 3×150 cm). One major immunoreactive (ir)-adrenomedullin was observed in the molecular weight of 5,000 to 6,000. The peptides in this fraction were further separated by CM ion exchange HPLC on a TSK CM-2SW column (8.0×300 mm, Tosoh). One major immunoreactive adrenomedullin was observed at the same position as that of human adrenomedullin. This fraction was finally purified by reverse phase HPLC on a phenyl column (4.6×250 mm, Vydac). The elution profiles of the absorbance at 210 nm and ir-adrenomedullin were in exact agreement with those of human adrenomedullin.

(B) Structural analysis of porcine adrenomedullin:

A hundred pmol of the porcine adrenomedullin obtained in item (A) was reduced and S-carboxymethylated (RCM) by the method described by Kangawa et al., Biochem. Biophys. Res. Commun., 118, 131–139 (1984). The obtained RCM-adrenomedullin was purified by reverse phase HPLC. The purified RCM-adrenomedullin was subjected to a gas phase sequencer (Model, 470A/120A, Applied Biosystems), and the amino acid sequence was determined up to the 37th residue. Separately, 100 pmol of porcine adrenomedullin was digested in 0.1M NH$_4$HCO$_3$ containing 0.01% Triton at a temperature of 37° C. with 500 ng of trypsin or chymotrypsin, thereby producing two peptide fragments. Each of the peptide fragments was separated by reverse phase HPLC on a Chemcosorb 3 ODS H semi-micro column (2.1×75 mm, Chemco, Osaka, Japan). Each fragment was sequenced by using a gas phase sequencer (model 470A/120A, Applied Biosystems), thereby determining the entire amino acid sequence of porcine adrenomedullin. Porcine adrenomedullin consisted of 52 amino acids and had an intramolecular disulfide bond. Tyr at the C-terminus was amidated.

The amino acid sequence of porcine adrenomedullin was identical to that of human adrenomedullin except that asparagine in the 40 position of human adrenomedullin was replaced with glycine in porcine adrenomedullin.

(Cloning of porcine adrenomedullin cDNA)

(A) Synthesis of a primer:

Based on the amino acid sequence of porcine adrenomedullin obtained in the above-mentioned manner, a DNA oligomer was synthesized. By the polymerase chain reaction (PCR) (Saiki, R. K. et al., Science, 239, 487–494 (1988)) by using the oligomer as a primer, a probe for screening of a cDNA library described below was produced.

The DNA oligomer to be used in PCR was designed and produced as follows. A mixed DNA oligomer covering the entire DNA sequences which can encode a certain region in a determined amino acid sequence can be designed by using various codons each corresponding to an amino acid residue. Practically, codons preferentially used in mammals were mainly used to synthesize DNA oligomers I and II (shown respectively in SEQ ID Nos. 3 and 4), and a DNA oligomer III (shown in SEQ ID No. 5), on the basis of the determined amino acids 3–8 and 35–41, respectively. The DNA oligomer III was based on the base sequence of the complementary chain of a gene encoding adrenomedullin. The DNA oligomers were chemically synthesized with a nucleic acid synthesizer (Pharmacia LKB Gene Assembler Plus, DNA Synthesizer) because they were short chain oligomers.

(B) Preparation of a template sample for PCR:

Since the results of the test for the presence of human adrenomedullin in each human tissue indicated that abundant adrenomedullin existed in the adrenal medulla, an adrenal medulla was considered suitable as a material for gene cloning.

RNA was extracted from a porcine adrenal medulla by the guanidine thiocyanate method (Chomczynski, P. et al., Anal. Biochem., 162, 156–159 (1987)). Poly(A)$^+$RNA was isolated on an oligo(dT)-cellulose column (Pharmacia). Double-stranded cDNA was produced from 5 $\mu$g of porcine adrenal medulla poly(A)$^+$RNA by the Gubler and Hoffman method. The double-stranded cDNA was ligated to an EcoRI adaptor, and size-fractionated on a Sephacryl S-300 column to obtain a fraction which was expected to contain the desired adrenomedullin. The obtained fraction was placed in $\lambda$ gt10 arms (Bethesda Research Laboratory) so as to be packaged in vitro, thereby producing a cDNA library.

(C) Amplification and isolation of porcine adrenomedullin cDNA by PCR:

By using a combination of the DNA oligomers I and III or a combination of the DNA oligomers II and III, which were obtained as described in item (A), an adrenomedullin cDNA fragment was amplified from the cDNA library obtained in item (B). In this PCR, AmpliTaq DNA polymerase available from Perkin Elmer Cetus, U.S.A., was used as an enzyme, and the composition of the used reaction solution was in accordance with their instructions. A thermal cycler (Perkin Elmer Cetus) was used as an amplifying device, and for amplification, a cycle of one minute at 94° C. and one minute at 37° C. was repeated 15 times and another cycle of 50 seconds at 94° C., 50 seconds at 48° C. and one minute at 72° C. was repeated 15 times.

The amplified cDNA fragment was labeled by the random primed method, and was used to probe the porcine adrenal medulla cDNA library by in situ plaque hybridization.

(D) Sequencing of porcine adrenomedullin cDNA:

A positive clone obtained by the plaque hybridization was plaque purified, and cDNA was taken out to provide a recombinant BlueScript plasmid. A clone including the longest cDNA insert was used for sequencing. A restriction fragment generated from the cDNA insert by digesting with an appropriate restriction endonuclease such as SmaI, NaeI and RsaI was resubcloned into BlueScript plasmid, and sequenced by the dyeprimer cycle sequencing method with an automated DNA sequencer (373A, Applied Biosystems).

The thus obtained entire sequence of the porcine adrenomedullin cDNA is shown in SEQ ID No: 4 and its amino acid sequence is shown in SEQ ID NO: 3.

[Example 5]
(Cloning of human adrenomedullin cDNA)

Human adrenomedullin cDNA was cloned using the same method as used in Example 4 by using the porcine adrenomedullin cDNA fragment obtained in item (C) of Example 4.

(A) Preparation of the cDNA library:

RNA was extracted from human PC by the guanidine thiocyanate method (Chomczynski, P. et al., Anal. Biochem., 162, 156–159 (1987)). Poly(A)$^+$RNA was isolated on an oligo(dT)-cellulose column (Pharmacia). Double-stranded cDNA was produced from the poly(A)$^+$RNA by the Gubler and Hoffman method. The double-stranded cDNA was ligated to an EcoRI adaptor, and size-fractionated on a Sephacryl S-300 column (Pharmacia) to obtain a fraction which was expected to contain the desired adrenomedullin. The obtained fraction was placed in $\lambda$ gt10 arms (Bethesda Research Laboratory) so as to be packaged in vitro, thereby producing a cDNA library.

(B) Sequencing of human adrenomedullin cDNA:

Human adrenomedullin cDNA was sequenced as follows.

The cDNA library obtained as above was screened by hybridization by using, as a probe, the porcine adrenomedullin cDNA fragment obtained in item (C) of Example 4.

A positive clone obtained by the plaque hybridization was purified, and cDNA was taken out to provide a recombinant BlueScript plasmid. A clone including the longest cDNA insert was used for sequencing. A restriction fragment generated from the cDNA insert by digesting with an appropriate restriction endonuclease such as SmaI, NaeI, RsaI and SacI was resubcloned into BlueScript plasmid, and sequenced by the dyeprimer cycle sequencing method or the dideoxy cycle sequencing method using an automated DNA sequencer (373A, Applied Biosystems).

The thus obtained cDNA sequence is shown in SEQ ID NO: 2 and its amino acid sequence is shown in SEQ ID NO: 1.

[Example 6]
(Structural analysis of proAM-N20)

ProAM-N20 is a portion corresponding to the N-terminal amino acid sequence of the proadrenomedullin of SEQ ID No. 1 determined in Example 5. More specifically, proAM-N20 is a peptide [(−73)–(−54)] corresponding to the amino acids (−73)–(−54) of SEQ ID No. 1. A computer search (PRF-SEQDB, Protein Research Foundation, Osaka, Japan) found no report on the same peptide sequence. Therefore, proAM-N20 was confirmed to be a novel peptide having a biological activity.

(Effect of proAM-N20 on catecholamine secretion)

ProAM-N20 was synthesized by the solid phase method with a peptide synthesizer (431A, Applied Biosystems), and purified by reverse phase HPLC.

(A) Cultured bovine adrenal medulla cells (four days old, $4 \times 10^6$ cells/dish) were washed with a KRP buffer, and incubated in 1 ml of a KRP buffer containing proAM-N20 ($10^{-6}$M) at a temperature of 37° C. for 10 minutes. A control was incubated in 1 ml of a KRP buffer alone under the same condition. The amounts of catecholamine in the obtained supernatants were measured by HPLC.

The amount of secreted catecholamine was 1.64 $\mu$g/$4 \times 10^6$ cells (n=2) when proAM-N20 was used, and was 2.56 $\mu$g/$4 \times 10^6$ cells in the control. In this manner, secretion of catecholamine was inhibited by proAM-N20.

(B) Bovine adrenal medulla cells were preincubated in the same manner as above in 1 ml of a KRP buffer containing proAM-N20 ($10^{-6}$M) at a temperature of 37° C. for 5 to 10 minutes. Then, carbachol ($10^{-4}$M) was added thereto for stimulation, and incubated for 10 minutes at a temperature of 37° C. A control was not preincubated with proAM-N20 but was stimulated by carbachol. The amount of secreted catecholamine in the obtained supernatant was measured by HPLC.

The amount of secreted catecholamine was 14.36 $\mu$g/$4 \times 10^6$ cells (n=2) in the control, whereas 11.31 $\mu$g/$4 \times 10^6$ cells when a 5 minute incubation was performed by using proAM-N20, and 9.19 $\mu$g/$4 \times 10^6$ cells when a 10 minute incubation was performed by using proAM-N20. In this manner, catecholamine secretion stimulated by carbachol was inhibited by pretreatment with proAM-N20.

[Example 7]
(RIA method utilizing proAM-N20 and its fragment)

A peptide [(-73)-(-54)]NH$_2$, a peptide N-Tyr-[(-73)-(-54)]NH$_2$ which is a peptide [(-73)-(-54)]NH$_2$ having Tyr at its N-terminus, a peptide [(-65)-(-54)]NH$_2$, a peptide [(-61)-(-54)]NH$_2$, and a peptide [(-58)-(-54)]NH$_2$ were synthesized by the solid phase method with a peptide synthesizer (Applied Biosystems, 431A), using phenoxy resin, and purified by reverse phase HPLC.

Ten mg of the peptide [(-73)-(-54)]NH$_2$ and 20 mg of bovine thyroglobulin were allowed to conjugate to each other by a carbodiimide method (Goodfriend et al., Science, 144, 1344–1346 (1964)). The obtained reaction mixture was dialyzed four times against 1 L of a saline and twice against 50 mM of sodium phosphate buffer (pH 7.4)/0.08M NaCl. The dialysate was emulsified with an equal volume of complete Freund's adjuvant, and the resultant was used for immunization of New Zealand white male rabbits. The antiserum obtained from the immunized animals was used in the following RIA. The peptide N-Tyr-[(-73)-(-54)]NH$_2$ was labeled by a lactoperoxidase method (Kitamura et al., Biochem. Biophys. Res. Commun., 161, 348–352 (1989)). The $^{125}$I-labeled peptide was purified by reverse phase HPLC using a TSK ODS 120A column (Tosoh) to use as a tracer.

Specifically, 100 μl of the peptide [(-73)-(-54)]NH$_2$ in a known concentration or in an unknown concentration and 200 μl of the antiserum obtained as above at a dilution of 1:66,500 were mixed to obtain an RIA reaction mixture. The mixture was incubated for 12 hours. Then, 100 μl of the $^{125}$I-labeled ligand (18,000 cpm) was added to the mixture. The resultant reaction mixture was incubated for 24 hours. Then, 100 μl of anti-rabbit IgG goat serum was added to the mixture. The resultant mixture was incubated for another 24 hours and centrifuged for 30 minutes at 2,000×g. The radioactivity of the obtained pellet was counted with the gamma counter (ARC-600, Aloka), and the assay was performed in duplicate at a temperature of 4° C. A standard curve was obtained from the values thus obtained. Half maximal inhibition of radioiodinated ligand binding by the peptide [(-73)-(-54)]NH$_2$ was observed at 10 fmol/tube.

The results of the above-mentioned RIA revealed that the antiserum had a reactivity against the peptide [(-73)-(-54)]NH$_2$ which is an antigen, a crossreactivity against the peptides [(-65)-(-54)]NH$_2$ and [(-61)-(-54)]NH$_2$ and no crossreactivity against the peptide [(-58)-(-54)]NH$_2$. Thus, the peptides [(-73)-(-54)]NH$_2$, [(-65)-(-54)]NH$_2$, and [(-61)-(-54)]NH$_2$ were found to be useful in the production of an antibody against proAM-N20.

(Distribution of proAM-N20 in each tissue)

From a human PC, an adrenal medulla, a heart (right atrium, left atrium, right ventricle, left ventricle), a lung, a kidney, a pancreas, an intestine, a liver, a spleen, and a brain cortex, 1.0 g of tissues were respectively taken out, and boiled in a 5-fold volume of water for 10 minutes to inactivate intrinsic protease. After cooling, glacial acetic acid was added to each so as to make the resultant mixture 1M. The mixture was homogenized with a polytron mixer at a temperature of 4° C. Then, the mixture was centrifuged at 24,000×g for 30 minutes, and the supernatant of the thus obtained extract was applied upon a Sep-Pak C-18 cartridge column (Waters), which had been previously equilibrated with 1M acetic acid. The materials adsorbed on the column were eluted with 4 ml of 50% acetonitrile containing 0.1% TFA. The immunoreactivity of proAM-N20 in the resultant solution was analyzed by gel filtration on a Sephadex G-50 column (Pharmarcia), reverse phase HPLC on a TSK ODS 120A column (4.6×150 mm, Tosoh) or ion exchange HPLC on a TSK CM-2SW column.

The presence of proAM-N20 in each of the above-mentioned human tissues was checked by RIA accompanied with identification of the peptide by reverse phase HPLC. The results are shown in Table 2 below.

TABLE 2

Regional distribution of ir-proAM-N20 in human tissue

| Region | ir-proAM-N20 (fmol/mg) |
|---|---|
| Adrenal medulla | 13.8 ± 7.93 |
| Pheochromocytoma | 12.3 ± 9.82 |
| Heart right atrium | 5.72 ± 1.11 |
| left atrium | 1.11 ± 0.62 |
| right ventricle | <0.1 |
| left ventricle | <0.1 |
| Lung | <0.1 |
| Kidney | <0.1 |
| Pancreas | <0.1 |
| Small intestine | <0.1 |
| Liver | <0.1 |
| Spleen | <0.1 |
| Brain cortex | <0.1 |

All values are mean±standard deviation for three to four samples.

As shown in Table 2, human adrenal medulla was found to include abundant proAM-N20 at an amount of 13.8±7.93 fmol/mg wet tissue. The atrium was also found to include abundant proAM-N20. A small amount of proAM-N20 was detected in the ventricle, lung, kidney, pancreas, intestine, liver, spleen, and brain cortex. The amount of proAM-N20 in 1 mg wet tissue of the right atrium was about 5 times that of the left atrium. However, the total amount of proAM-N20 in the ventricles was smaller than the amount in the atriums. The distribution of proAM-N20 was very similar to that of adrenomedullin. proAM-N20 was included in a precursor of adrenomedullin together with adrenomedullin. There is a possibility that proAM-N20 is also related to the regulation of the circulating system, as in adrenomedullin, CGRP, BNP, ANP which is localized in the ventricles.

The concentration of proAM-N20 of the human adrenal medulla was 12.3±9.82 fmol/mg wet tissue. However, the variation of values in each sample is large, which is considered to be dependent upon the degree of differentiation of a tumor cell generating proAM-N20.

[Example 8]
(Effect of proAM-N(10–20) on sodium channel)

ProAM-N(10–20) is a portion corresponding to the amino acid N-terminal sequence of proadrenomedullin in SEQ ID No. 1 determined in Example 5. More specifically, it is a peptide [(-64)-(-54)] corresponding to the amino acids (-64)-(-54) of SEQ ID No. 1. ProAM-N(10–20) was synthesized by the solid phase method with a peptide synthesizer (431A, Applied Biosystems), and purified by reverse phase HPLC.

Cultured bovine adrenal medulla cells (four days old, 4×10$^6$ cells/dish) were washed with a KRP buffer, and preincubated in 1 ml of a KRP buffer containing proAM-N (10–20) (10$^{-6}$M) or 1 ml of a KRP buffer containing proAM-N20 (10$^{-6}$M) at a temperature of 37° C. for 5 to 10 minutes. Then, carbachol (300 μM) was added thereto for stimulation, and incubated for 2 minutes at a temperature of 37° C. The amount of $^{22}$Na which flowed into the cells was measured in each sample. A control was not subjected to the pre incubation, and was only stimulated by carbachol.

The amount of $^{22}$Na was 99.8 nmol/dish (n=2) in the control, whereas it was 29.1 nmol/dish (n=2) when proAM- N(10–20) was used, and was 70.5 nmol/dish (n=2) when proAM-N20 was used. In this manner, the flow of $^{22}$Na into cells was inhibited by proAM-N(10–20) by 70% and proAM-N20 by 30%.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

The following specific sequence information and descriptions are provided in order to comply with the formal requirements of the submission of sequence data to the United States Patent and Trademark Office and are not intended to limit the scope of what the inventors regard as their invention. Variations in sequences which will become apparent to those skilled in the art upon review of this disclosure and which are encompassed by the attached claims are intended to be within the scope of the present invention. Further, it should be noted that efforts have been made to insure accuracy with respect to the specific sequences and characteristic description information describing such sequences, but some experimental error and/or deviation should be accounted for.

What is claimed is:

1. An isolated DNA molecule comprising a nucleotide base sequence encoding a peptide which comprises an amino acid sequence selected from the group consisting of an amino acid sequence from Ser in the 13 position to Tyr in the 52 position of SEQ ID NO: 1, an amino acid sequence from Tyr in the 1 position to Tyr in the 52 position of SEQ ID NO: 1, an amino acid sequence from Ala in the −73 position to Tyr in the 52 position of SEQ ID NO: 1, an amino acid sequence from Met in the −94 position to Leu in the 91 position of SEQ ID NO: 1, an amino acid sequence from Gln in the 3 position to Arg in the 12 position of SEQ ID NO: 1, an amino acid sequence from Tyr in the 1 position to Arg in the 12 position of SEQ ID NO: 1, an amino acid sequence from Ile in the 47 position to Tyr in the 52 position of SEQ ID NO: 1, an amino acid sequence from Ser in the 45 position to Tyr in the 52 position of SEQ ID NO: 1, an amino acid sequence from Asn in the 40 position to Tyr in the 52 position of SEQ ID NO: 1, an amino acid sequence from Arg in the −64 position to Arg in the −54 position of SEQ ID NO: 1, and an amino acid sequence from Ala in the −73 position to Arg in the −54 position of SEQ ID NO: 1, an amino acid sequence from Trp in the −61 position to Arg in the −54 position of SEQ ID NO: 1, and an amino acid sequence from Phe in the −65 position to Arg in the −54 position of SEQ ID NO: 1.

2. An isolated DNA molecule according to claim 1 comprising a base sequence from A in the 483 position to C in the 602 position of SEQ ID NO: 2.

3. An isolated DNA molecule according to claim 1 comprising a base sequence from A in the 483 position to C in the 605 position of SEQ ID NO: 2.

4. An isolated DNA molecule according to claim 1 comprising a base sequence from T in the 447 position to C in the 602 position of SEQ ID NO: 2.

5. An isolated DNA molecule according to claim 1 comprising a base sequence from T in the 447 position to C in the 605 position of SEQ ID NO: 2.

6. An isolated DNA molecule according to claim 1 comprising a base sequence from G in the 228 position to C in the 602 position of SEQ ID NO: 2.

7. An isolated DNA molecule according to claim 1 comprising a base sequence from G in the 228 position to C in the 605 position of SEQ ID NO: 2.

8. An isolated DNA molecule according to claim 1 comprising a base sequence from A in the 165 position to T in the 719 position of SEQ ID NO: 2.

9. An isolated DNA molecule according to claim 1 comprising a base sequence from C in the 255 position to T in the 287 position of SEQ ID NO: 2.

10. An isolated DNA molecule according to claim 1 comprising a base sequence from C in the 255 position to G in the 290 position of SEQ ID NO: 2.

11. An isolated DNA molecule according to claim 1 comprising a base sequence from G in the 228 position to T in the 287 position of SEQ ID NO: 2.

12. An isolated DNA molecule according to claim 1 comprising a base sequence from G in the 228 position to G in the 290 position of SEQ ID No: 2.

13. An isolated DNA molecule according to claim 1 comprising a base sequence from T in the 264 position to T in the 287 position of SEQ ID NO: 2.

14. An isolated DNA molecule according to claim 1 comprising a base sequence from T in the 252 position to T in the 287 position of SEQ ID NO: 2.

15. An expression vector having any one of the DNA sequences of claims 1 through 14.

16. A transformant obtained by introducing the expression vector of claim 15 into a host.

17. A production method for a peptide which comprises an amino acid sequence selected from the group consisting of an amino acid sequence from Ser in the 13 position to Tyr in the 52 position of SEQ ID NO: 1, an amino acid sequence from Tyr in the 1 position to Tyr in the 52 position of SEQ ID NO: 1, an amino acid sequence from Ala in the −73 position to Tyr in the 52 position of SEQ ID NO: 1, an amino acid sequence from Met in the −94 position to Leu in the 91 position of SEQ ID NO: 1, an amino acid sequence from Gln in the 3 position to Arg in the 12 position of SEQ ID NO: 1, an amino acid sequence from Tyr in the 1 position to Arg in the 12 position of SEQ ID NO: 1, an amino acid sequence from Ile in the 47 position to Tyr in the 52 position of SEQ ID NO: 1, an amino acid sequence from Ser in the 45 position to Tyr in the 52 position of SEQ ID NO: 1, and an amino acid sequence from Asn in the 40 position to Tyr in the 52 position of SEQ ID NO: 1, comprising the steps of:
    culturing the transformant of claim 16 in a medium; and
    collecting the generated peptide from the medium.

18. A production method according to claim 17 further comprising a step of amidating the carboxyl terminus of the collected peptide.

\* \* \* \* \*

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 185 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Met  Lys  Leu  Val  Ser  Val  Ala  Leu  Met  Tyr  Leu  Gly  Ser  Leu  Ala  Phe
              -90            -85                           -80

Leu  Gly  Ala  Asp  Thr  Ala  Arg  Leu  Asp  Val  Ala  Ser  Glu  Phe  Arg  Lys
              -75                      -70                      -65

Lys  Trp  Asn  Lys  Trp  Ala  Leu  Ser  Arg  Gly  Lys  Arg  Glu  Leu  Arg  Met
         -60                      -55                      -50

Ser  Ser  Ser  Tyr  Pro  Thr  Gly  Leu  Ala  Asp  Val  Lys  Ala  Gly  Pro  Ala
    -45                      -40                 -35

Gln  Thr  Leu  Ile  Arg  Pro  Gln  Asp  Met  Lys  Gly  Ala  Ser  Arg  Ser  Pro
-30                      -25                 -20                          -15

Glu  Asp  Ser  Ser  Pro  Asp  Ala  Ala  Arg  Ile  Arg  Val  Lys  Arg  Tyr  Arg
              -10                      -5                             1

Gln  Ser  Met  Asn  Asn  Phe  Gln  Gly  Leu  Arg  Ser  Phe  Gly  Cys  Arg  Phe
         5                      10                      15

Gly  Thr  Cys  Thr  Val  Gln  Lys  Leu  Ala  His  Gln  Ile  Tyr  Gln  Phe  Thr
    20                      25                      30

Asp  Lys  Asp  Lys  Asp  Asn  Val  Ala  Pro  Arg  Ser  Lys  Ile  Ser  Pro  Gln
35                       40                      45                         50

Gly  Tyr  Gly  Arg  Arg  Arg  Arg  Arg  Ser  Leu  Pro  Glu  Ala  Gly  Pro  Gly
              55                      60                         65

Arg  Thr  Leu  Val  Ser  Ser  Lys  Pro  Gln  Ala  His  Gly  Ala  Pro  Ala  Pro
              70                      75                         80

Pro  Ser  Gly  Ser  Ala  Pro  His  Phe  Leu
         85                      90
```

( 2 ) INFORMATION FOR SEQ ID NO:2:

( i ) SEQUENCE CHARACTERISTICS:
        ( A ) LENGTH: 1457 base pairs
        ( B ) TYPE: nucleic acid
        ( C ) STRANDEDNESS: double
        ( D ) TOPOLOGY: linear (ii) MOLECULE TYPE: cDNA to mRNA (ix) FEATURE:
    (A) NAME/KEY: CDS
    (B) LOCATION: 165..719

(xi) SEQUENCE DESCRIPTION: SEQ ID NO:2:

```
GGCACGAGCT GGATAGAACA GCTCAAGCCT TGCCACTTCG GGCTTCTCAC TGCAGCTGGG        60

CTTGGACTTC GGAGTTTTGC CATTGCCAGT GGGACGTCTG AGACTTTCTC CTTCAAGTAC       120

TTGGCAGATC ACTCTCTTAG CAGGGTCTGC GCTTCGCAGC CGGG ATG AAG CTG GTT       176
                                                 Met Lys Leu Val

TCC GTC GCC CTG ATG TAC CTG GGT TCG CTC GCC TTC CTA GGC GCT GAC        224
Ser Val Ala Leu Met Tyr Leu Gly Ser Leu Ala Phe Leu Gly Ala Asp
-90             -85             -80             -75

ACC GCT CGG TTG GAT GTC GCG TCG GAG TTT CGA AAG AAG TGG AAT AAG        272
Thr Ala Arg Leu Asp Val Ala Ser Glu Phe Arg Lys Lys Trp Asn Lys
            -70             -65             -60

TGG GCT CTG AGT CGT GGG AAG AGG GAA CTG CGG ATG TCC AGC AGC TAC        320
Trp Ala Leu Ser Arg Gly Lys Arg Glu Leu Arg Met Ser Ser Ser Tyr
        -55             -50             -45

CCC ACC GGG CTC GCT GAC GTG AAG GCC GGG CCT GCC CAG ACC CTT ATT        368
Pro Thr Gly Leu Ala Asp Val Lys Ala Gly Pro Ala Gln Thr Leu Ile
    -40             -35             -30

CGG CCC CAG GAC ATG AAG GGT GCC TCT CGA AGC CCC GAA GAC AGC AGT        416
Arg Pro Gln Asp Met Lys Gly Ala Ser Arg Ser Pro Glu Asp Ser Ser
-25             -20             -15

CCG GAT GCC GCC CGC ATC CGA GTC AAG CGC TAC CGC CAG AGC ATG AAC        464
Pro Asp Ala Ala Arg Ile Arg Val Lys Arg Tyr Arg Gln Ser Met Asn
-10             -5               1               5

AAC TTC CAG GGC CTC CGG AGC TTT GGC TGC CGC TTC GGG ACG TGC ACG        512
Asn Phe Gln Gly Leu Arg Ser Phe Gly Cys Arg Phe Gly Thr Cys Thr
            10              15              20

GTG CAG AAG CTG GCA CAC CAG ATC TAC CAG TTC ACA GAT AAG GAC AAG        560
Val Gln Lys Leu Ala His Gln Ile Tyr Gln Phe Thr Asp Lys Asp Lys
        25              30              35

GAC AAC GTC GCC CCC AGG AGC AAG ATC AGC CCC CAG GGC TAC GGC CGC        608
Asp Asn Val Ala Pro Arg Ser Lys Ile Ser Pro Gln Gly Tyr Gly Arg
    40              45              50

CGG CGC CGG CGC TCC CTG CCC GAG GCC GGC CCG GGT CGG ACT CTG GTG        656
Arg Arg Arg Arg Ser Leu Pro Glu Ala Gly Pro Gly Arg Thr Leu Val
55              60              65              70

TCT TCT AAG CCA CAA GCA CAC GGG GCT CCA GCC CCC CCG AGT GGA AGT        704
Ser Ser Lys Pro Gln Ala His Gly Ala Pro Ala Pro Pro Ser Gly Ser
            75              80              85

GCT CCC CAC TTT CTT TAGGATTTAG GCGCCCATGG TACAAGGAAT AGTCGCGCAA        759
Ala Pro His Phe Leu
            90

GCATCCCGCT GGTGCCTCCC GGGACGAAGG ACTTCCCGAG CGGTGTGGGG ACCGGGCTCT       819

GACAGCCCTG CGGAGACCCT GAGTCCGGGA GGCACCGTCC GGCGGCGAGC TCTGGCTTTG       879

CAAGGGCCCC TCCTTCTGGG GGCTTCGCTT CCTTAGCCTT GCTCAGGTGC AAGTGCCCCA       939

GGGGGCGGGG TGCAGAAGAA TCCGAGTGTT TGCCAGGCTT AAGGAGAGGA GAAACTGAGA       999

AATGAATGCT GAGACCCCCG GAGCAGGGGT CTGAGCCACA GCCGTGCTCG CCCACAAACT      1059

GATTTCTCAC GGCGTGTCAC CCCACCAGGG CGCAAGCCTC ACTATTACTT GAACTTTCCA      1119

AAACCTAAAG AGGAAAAGTG CAATGCGTGT TGTACATACA GAGGTAACTA TCAATATTTA      1179

AGTTTGTTGC TGTCAAGATT TTTTTTGTAA CTTCAAATAT AGAGATATTT TTGTACGTTA      1239

TATATTGTAT TAAGGGCATT TTAAAAGCAA TTATATTGTC CTCCCCTATT TTAAGACGTG      1299
```

AATGTCTCAG CGAGGTGTAA AGTTGTTCGC CGCGTGGAAT GTGAGTGTGT TTGTGTGCAT 1359

GAAAGAGAAA GACTGATTAC CTCCTGTGTG GAAGAAGGAA ACACCGAGTC TCTGTATAAT 1419

CTATTTACAT AAAATGGGTG ATATGCGAAC AGCAAACC 1457

( 2 ) INFORMATION FOR SEQ ID NO:3:

( i ) SEQUENCE CHARACTERISTICS:
        ( A ) LENGTH: 188 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met  Lys  Leu  Val  Pro  Val  Ala  Leu  Met  Tyr  Leu  Gly  Ser  Leu  Ala  Phe
          -90                     -85                     -80

Leu  Gly  Ala  Asp  Thr  Ala  Arg  Leu  Asp  Val  Ala  Ala  Glu  Phe  Arg  Lys
               -75                     -70                     -65

Lys  Trp  Asn  Lys  Trp  Ala  Leu  Ser  Arg  Gly  Lys  Arg  Glu  Leu  Arg  Leu
          -60                     -55                     -50

Ser  Ser  Ser  Tyr  Pro  Thr  Gly  Ile  Ala  Asp  Leu  Lys  Ala  Gly  Pro  Ala
     -45                     -40                     -35

Gln  Thr  Val  Ile  Arg  Pro  Gln  Asp  Val  Lys  Gly  Ser  Ser  Arg  Ser  Pro
-30                      -25                     -20                     -15

Gln  Ala  Ser  Ile  Pro  Asp  Ala  Ala  Arg  Ile  Arg  Val  Lys  Arg  Tyr  Arg
               -10                      -5                              1

Gln  Ser  Met  Asn  Asn  Phe  Gln  Gly  Leu  Arg  Ser  Phe  Gly  Cys  Arg  Phe
          5                       10                      15

Gly  Thr  Cys  Thr  Val  Gln  Lys  Leu  Ala  His  Gln  Ile  Tyr  Gln  Phe  Thr
          20                      25                      30

Asp  Lys  Asp  Lys  Asp  Gly  Val  Ala  Pro  Arg  Ser  Lys  Ile  Ser  Pro  Gln
35                       40                      45                      50

Gly  Tyr  Gly  Arg  Arg  Arg  Arg  Arg  Ser  Leu  Pro  Glu  Ala  Ser  Leu  Gly
               55                      60                      65

Arg  Thr  Leu  Arg  Ser  Gln  Glu  Pro  Gln  Ala  His  Gly  Ala  Pro  Ala  Ser
               70                      75                      80

Pro  Ala  His  Gln  Val  Leu  Ala  Thr  Leu  Phe  Arg  Ile
          85                      90
```

( 2 ) INFORMATION FOR SEQ ID NO:4:

( i ) SEQUENCE CHARACTERISTICS:
        ( A ) LENGTH: 1493 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 148..711

( x i ) SEQUENCE DESCRIPTION: SEQ ID NO:4:

GCGGAACAGC TCGAGCCTTG CCACCTCTAG TTTCTTACCA CAGCTTGGAC GTCGGGGTTT 60

TGCCACTGCC AGAGGGACGT CTCAGACTTC ATCTTCCCAA ATCTTGGCAG ATCACCCCCT 120

TAGCAGGGTC TGCACATCTC AGCCGGG ATG AAG CTG GTT CCC GTA GCC CTC 171
                                  Met Lys Leu Val Pro Val Ala Leu
                                       -90

```
ATG TAC CTG GGC TCG CTC GCC TTC CTG GGC GCT GAC ACA GCT CGG CTC     219
Met Tyr Leu Gly Ser Leu Ala Phe Leu Gly Ala Asp Thr Ala Arg Leu
    -85             -80                  -75

GAC GTG GCG GCA GAG TTC CGA AAG AAA TGG AAT AAG TGG GCT CTA AGT     267
Asp Val Ala Ala Glu Phe Arg Lys Lys Trp Asn Lys Trp Ala Leu Ser
-70             -65                  -60                  -55

CGT GGA AAA AGA GAA CTT CGG CTG TCC AGC AGC TAC CCC ACC GGG ATC     315
Arg Gly Lys Arg Glu Leu Arg Leu Ser Ser Ser Tyr Pro Thr Gly Ile
                -50                  -45                  -40

GCC GAC TTG AAG GCC GGG CCT GCC CAG ACT GTC ATT CGG CCC CAG GAT     363
Ala Asp Leu Lys Ala Gly Pro Ala Gln Thr Val Ile Arg Pro Gln Asp
            -35                  -30                  -25

GTG AAG GGC TCC TCT CGC AGC CCC CAG GCC AGC ATT CCG GAT GCA GCC     411
Val Lys Gly Ser Ser Arg Ser Pro Gln Ala Ser Ile Pro Asp Ala Ala
        -20                  -15                  -10

CGC ATC CGA GTC AAG CGC TAC CGC CAG AGT ATG AAC AAC TTC CAG GGC     459
Arg Ile Arg Val Lys Arg Tyr Arg Gln Ser Met Asn Asn Phe Gln Gly
     -5                   1                   5                  10

CTG CGG AGC TTC GGC TGT CGC TTT GGG ACG TGC ACC GTG CAG AAG CTG     507
Leu Arg Ser Phe Gly Cys Arg Phe Gly Thr Cys Thr Val Gln Lys Leu
                 15                  20                  25

GCG CAC CAG ATC TAC CAG TTC ACG GAC AAA GAC AAG GAC GGC GTC GCC     555
Ala His Gln Ile Tyr Gln Phe Thr Asp Lys Asp Lys Asp Gly Val Ala
             30                  35                  40

CCC CGG AGC AAG ATC AGC CCC CAG GGC TAC GGC CGC CGG CGC CGA CGC     603
Pro Arg Ser Lys Ile Ser Pro Gln Gly Tyr Gly Arg Arg Arg Arg Arg
         45                  50                  55

TCT CTG CCC GAA GCC AGC CTG GGC CGG ACT CTG AGG TCC CAG GAG CCA     651
Ser Leu Pro Glu Ala Ser Leu Gly Arg Thr Leu Arg Ser Gln Glu Pro
     60                  65                  70

CAG GCG CAC GGG GCC CCG GCC TCC CCG GCG CAT CAA GTG CTC GCC ACT     699
Gln Ala His Gly Ala Pro Ala Ser Pro Ala His Gln Val Leu Ala Thr
 75                  80                  85                  90

CTC TTT AGG ATT TAGGCGCCTA CTGTGGCAGC AGCGAACAGT CGCGCATGCA         751
Leu Phe Arg Ile
TCATGCCGGC GCTTCCTGGG GCGGGGGGCT TCCCGGAGCC GAGCCCCTCA GCGGCTGGGG   811

CCCGGGCAGA GACAGCATTG AGAGACCGAG AGTCCGGGAG GCACAGACCA GCGGCGAGCC   871

CTGCATTTTC AGGAACCCGT CCTGCTTGGA GGCAGTGTTC TCTTCGGCTT AATCCAGCCC   931

GGGTCCCCGG GTGGGGGTGG AGGGTGCAGA GGAATCCAAA GGAGTGTCAT CTGCCAGGCT   991

CACGGAGAGG AGAAACTGCG AAGTAAATGC TTAGACCCCC AGGGGCAAGG GTCTGAGCCA  1051

CTGCCGTGCC GCCCACAAAC TGATTTCTGA AGGGGAATAA CCCCAACAGG GCGCAAGCCT  1111

CACTATTACT TGAACTTTCC AAAACCTAGA GAGGAAAAGT GCAATGTATG TTGTATATAA  1171

AGAGGTAACT ATCAATATTT AAGTTTGTTG CTGTCAAGAT TTTTTTTTGT AACTTCAAAT  1231

ATAGAGATAT TTTTGTACGT TATATATTGT ATTAAGGGCA TTTTAAAACA ATTGTATTGT  1291

TCCCCTCCCC TCTATTTTAA TATGTGAATG TCTCAGCGAG GTGTAACATT GTTTGCTGCG  1351

CGAAATGTGA GAGTGTGTGT GTGTGTGTGC GTGAAAGAGA GTCTGGATGC CTCTTGGGGA  1411

AGAAGAAAAC ACCATATCTG TATAATCTAT TTACATAAAA TGGGTGATAT GCGAAGTAGC  1471

AAACCAATAA ACTGTCTCAA TG                                          1493
```

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear (i i) MOLECULE TYPE: other nucleic acid
  (A) DESCRIPTION: /desc = "synthetic DNA"

(x i) SEQUENCE DESCRIPTION: SEQ ID NO:5:

CARTCNATGA AYAAYTTYCA RGG  23

(2) INFORMATION FOR SEQ ID NO:6:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "synthetic DNA"

(x i) SEQUENCE DESCRIPTION: SEQ ID NO:6:

CARAGYATGA AYAAYTTYCA RGG  23

(2) INFORMATION FOR SEQ ID NO:7:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "synthetic DNA"

(x i) SEQUENCE DESCRIPTION: SEQ ID NO:7:

ACNCCRTCYT TRTCYTTRTC  20

(2) INFORMATION FOR SEQ ID NO:8:

(i) SEQUENCE CHARACTERISTICS:
    (A) LENGTH: 37 amino acids
    (B) TYPE: amino acid
    (D) TOPOLOGY: linear (i i) MOLECULE TYPE: protein (x i) SEQUENCE DESCRIPTION: SEQ ID NO:8:

Ala Cys Asp Thr Ala Thr Cys Val Thr His Arg Leu Ala Gly Leu Leu Ser
 1               5                  10                  15
Arg Ser Gly Gly Val Val Lys Asn Asn Phe Val Pro Thr Asn Val Gly Ser
            20                  25                  30
Lys Ala Phe
 35

(2) INFORMATION FOR SEQ ID NO:9:

(i) SEQUENCE CHARACTERISTICS:
    (A) LENGTH: 37 amino acids
    (B) TYPE: amino acid
    (D) TOPOLOGY: linear (i i) MOLECULE TYPE: protein (x i) SEQUENCE DESCRIPTION: SEQ ID NO:9:

Ala Cys Asn Thr Ala Thr Cys Val Thr His Arg Leu Ala Gly Leu Leu Ser
 1               5                  10                  15
Arg Ser Gly Gly Met Val Lys Ser Asn Phe Val Pro Thr Asn Val Gly Ser
            20                  25                  30
Lys Ala Phe (2) INFORMATION FOR SEQ ID NO:10:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO:10:

```
Lys Cys Asn Thr Ala Thr Cys Ala Thr Gln Arg Leu Ala Asn Phe Leu Val
 1                   5                  10                  15
His Ser Ser Asn Asn Phe Gly Ala Ile Leu Ser Ser Thr Asn Val Gly Ser
         20                  25                  30
Asn Thr Tyr
 35
```